United States Patent
Rubin et al.

(10) Patent No.: US 7,803,552 B2
(45) Date of Patent: Sep. 28, 2010

(54) BIOMARKERS FOR PREDICTING PROSTATE CANCER PROGRESSION

(75) Inventors: Mark A. Rubin, Cambridge, MA (US); Francesca DeMichelis, Cambridge, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 12/607,036

(22) Filed: Oct. 27, 2009

(65) Prior Publication Data

US 2010/0137164 A1 Jun. 3, 2010

Related U.S. Application Data

(62) Division of application No. 11/361,517, filed on Feb. 24, 2006, now Pat. No. 7,666,595.

(60) Provisional application No. 60/656,489, filed on Feb. 25, 2005.

(51) Int. Cl.
C12Q 1/68 (2006.01)
G01N 33/53 (2006.01)
C07H 21/02 (2006.01)
C07K 14/00 (2006.01)

(52) U.S. Cl. .................... 435/6; 435/7.1; 536/23.1; 536/23.5; 536/24.3; 530/350

(58) Field of Classification Search .................. None
See application file for complete search history.

(56) References Cited

U.S. PATENT DOCUMENTS

| | | | |
|---|---|---|---|
| 5,972,615 A | 10/1999 | An et al. | |
| 6,171,796 B1 | 1/2001 | An et al. | |
| 6,703,202 B2 | 3/2004 | McGrath et al. | |
| 2002/0192699 A1 | 12/2002 | Zhang et al. | |
| 2003/0113762 A1 | 6/2003 | Warrington | |
| 2003/0134280 A1 | 7/2003 | Munger et al. | |
| 2003/0134324 A1 | 7/2003 | Munger et al. | |
| 2003/0152980 A1 | 8/2003 | Golub et al. | |
| 2003/0215835 A1 | 11/2003 | Sun et al. | |
| 2004/0224306 A1 | 11/2004 | Kuhne et al. | |
| 2006/0063214 A1 | 3/2006 | Alper | |
| 2007/0128639 A1 | 6/2007 | Chinnaiyan et al. | |

OTHER PUBLICATIONS

Baron et al., "Fatty acid synthase: a metabolic oncogene in prostate cancer", *J. Cell Biochem.*, 2004, 91:47-953.
Bismar et al., "Defining Aggressive Prostate Cancer Using a 12 Gene Model", *Neoplasia*, 2006, 8:59-68.
Bracken et al., "EZH2 is downstream of the pRB-E2F pathway, essential for proliferation and amplified in cancer", *EMBO J.*, 2003, 22: 5323-5335.
Brawn et al., "Prostate-specific antigen levels from completely sectioned, clinically benign, whole prostates", *Cancer*, 1991, 68:1592-1599.
Bubendorf et al., "Ki67 labelling index: an independent predictor of progression in prostate cancer treated by radical prostatectomy", *J. Pathol.*, 1996, 178: 437-441.
Bussemakers et al., "Decreased expression of E-cadherin in the progression of rat prostatic cancer", *Cancer Res.*, 1992, 52: 2916-2922.
Cheville et al., "Expression of p27kip1 in prostatic adenocarcinoma", *Mod. Pathol.*, 1998, 11: 324-328.
Cher et al., "Comparative genomic hybridization, allelic imbalance, and fluorescence in situ hybridization on chromosome 8 in prostate cancer", *Genes Chromosomes Cancer*, 1994, 11: 153-162.
Choo et al., "Feasibility study: watchful waiting for localized low to intermediate grade prostate carcinoma with selective delayed intervention based on prostate specific antigen, histological and/or clinical progression", *J. Urol.*, 2002, 167: 1664-1669.
Cordon-Cardo et al., "Distinct altered patterns of p27KIP1 gene expression in benign prostatic hyperplasia and prostatic carcinoma", *J. Natl. Cancer Inst.*, 1998, 90: 1284-1291.
De Marzo et al., "E-cadherin expression as a marker of tumor aggressiveness in routinely processed radical prostatectomy specimens", *Urology*, 1999, 53:707-713.
De Marzo et al., "Pathological and molecular aspects of prostate cancer", *Lancet*, 2003, 361: 955-964.
Dhanasekaran et al., "Delineation of prognostic biomarkers in prostate cancer", *Nature*, 2001, 412: 822-826.
Eisen et al., "Cluster analysis and display of genome-wide expression pattern", *Proc. Natl. Acad. Sci. USA*, 1998, 95: 14863-14868.
Epstein et al., "OA-519 (fatty acid synthase) as an independent predictor of pathologic state in adenocarcinoma of the prostate", *Urology*, 1995, 45: 81-86.
Etzioni et al., "Overdiagnosis due to prostate-specific antigen screening: lessons from U.S. prostate cancer incidence trends ", *J. Natl. Cancer Inst.*, 2002, 94: 981-990.
Farhana et al., "Cyclin B and E2F-1 expression in prostate carcinoma cells treated with the novel retinoid CD437 are regulated by the ubiquitin-mediated pathway", *Cancer Res.*, 2002, 62: 3842-3849.

(Continued)

*Primary Examiner*—Eileen B O Hara
(74) *Attorney, Agent, or Firm*—Choate Hall & Stewart LLP; Fangli Chen

(57) ABSTRACT

The present invention relates to the identification and use of gene expression profiles with clinical relevance to prostate cancer. In particular, the invention provides the identity of genes whose expression, at the transcriptional and protein levels, is correlated with prostate cancer progression. Methods and kits are described for using these gene expression profiles in the study and/or diagnosis of prostate cancer diseases, in the prediction of prostate cancer progression, and in the selection and/or monitoring of treatment regimens. The invention also relates to the screening of drugs that target these genes or their protein products, in particular for the development of therapeutics for modulating prostate cancer progression.

32 Claims, 20 Drawing Sheets
(7 of 20 Drawing Sheet(s) Filed in Color)

OTHER PUBLICATIONS

Foster et al., "Transcription factor E2F3 overexpressed in prostate cancer independently predicts clinical outcome", *Oncogene*, 2004, 23: 5871-5879.

Gelmann, "Molecular biology of the androgen receptor", *J. Clin. Oncol.*, 2002, 20: 3001-3015.

Glinsky et al., "Gene expression profiling predicts clinical outcome of prostate cancer", *J. Clin. Invest.*, 2004, 113: 913-923.

Golub et al., "Molecular classification of cancer: class discovery and class prediction by gene expression monitoring", *Science*, 1999, 286: 531-537.

Guo et al., "Loss of the cyclin-dependent kinase inhibitor p27(Kip1) protein in human prostate cancer correlates with tumor grade", *Clin. Cancer Res.*, 1997, 3: 2269-2274.

Hale et al., "Zinc alpha-2-glycoprotein is expressed by malignant prostatic epithelium and may serve as a potential serum marker for prostate cancer", *Clin. Cancer Res.*, 2001, 7: 846-853.

Hofer et al., "The role of metastasis-associated protein 1 in prostate cancer progression", *Cancer Res.*, 2004, 64: 825-829.

Ihaka and R.R. Gentleman, Journal of Computational and Graphical Statistics, 1996, 5:299-314.

International Search Report in Corresponding PCT application No. PCT/US2006/006527.

Jiang et al., "Joint analysis of two microarray gene-expression data sets to select lung adenocarcinoma marker genes", *BMC Bioinformatics*, 2004, 5: 81.

Jiang et al., "P504S: a new molecular marker for the detection of prostate carcinoma", *Am. J. Surg. Pathol.*, 2001, 25: 1397-1404.

Johansson et al., "Natural history of localised prostatic cancer. A population-based study in 223 untreated patients", *Lancet*, 1989, 1: 799-803.

Kleer et al., "EZH2 is a marker of aggressive breast cancer and promotes neoplastic transformation of breast epithelial cells", *Proc. Natl. Acad. Sci. USA*, 2003, 100: 11606-11611.

Krajewska et al., "Elevated expression of inhibitor of apoptosis proteins in prostate cancer", *Clinical Cancer Research*, 2003, 9: 4914-4925.

Kuefer et al., "alpha-Methylacyl-CoA racemase: expression levels of this novel cancer biomarker depend on tumor differentiation", *Am. J. Pathol.*, 2002, 161: 841-848.

Lapointe J et al., "Gene expression profiling identifies clinically relevant subtypes of prostate cancer", *Proc. Natl. Acad. Sci. USA*, 2004, 101: 811-816.

Latulippe et al., "Comprehensive gene expression analysis of prostate cancer reveals distinct transcriptional programs associated with metastatic disease", *Cancer Res.*, 2002, 62: 4499-4506.

Li and W.H. Wong, "Model-based analysis of oligonucleotide arrays: expression index computation and outlier detection", *Proc. Acad. Sci. USA*, 2001, 98: 31-36.

Luo et al., "Human prostate cancer and benign prostatic hyperplasia: molecular dissection by gene expression profiling", *Cancer Res.*, 2001, 61: 483-4688.

Luo et al., "Alpha-methylacyl-CoA racemase: a new molecular marker for prostate cancer", *Cancer Res.*, 2002, 62 : 2220-2226.

Luo et al., "Gene expression analysis of prostate cancers", *Mol. Carcinog.*, 2002, 33: 25-35.

Macoska et al., "Extensive genetic alterations in prostate cancer revealed by dual PCR and FISH analysis", *Genes Chromosomes Cancer*, 1993, 8: 88-97.

Macoska et al., "Fluorescence in situ hybridization analysis of 8p allelic loss and chromosome 8 instability in human prostate cancer", *Cancer Res.*, 1994, 54: 3824-3830.

Macoska et al., "Evidence for three tumor suppressor gene loci on chromosome 8p in human prostate cancer", *Cancer Res.*, 1995, 55: 5390-5395.

Macoska et al., "8p22 loss concurrent with 8c gain is associated with poor outcome in prostate cancer", *Urology*, 2000, 55: 776-782.

Magee et al., "Expression profiling reveals hepsin overexpression in prostate cancer", *Cancer Res.*, 2001, 61: 5692-5696.

Manley et al., "Relational database structure to manage high-density tissue microarray data and images for pathology studies focusing on clinical outcome: the prostate specialized program of research excellence model", *Am. J. Pathol.*, 2001, 159: 837-843.

Martin et al., "Quantitative proteomic analysis of proteins released by neoplastic prostate epithelium", *Cancer Res.*, 2004, 64: 347-355.

Monti et al., "Molecular profiling of diffuse large B-cell lymphoma identifies robust subtypes including one characterized by host inflammatory response", *Blood*, 2005, 105: 1851-1861.

Mootha et al., "PGC-1alpha-responsive genes involved in oxidative phosphorylation are coordinately downregulated in human diabetes", *Nat. Genet.*, 2003, 34: 267-273.

Mu and C. Chang, "TR3 orphan nuclear receptor mediates apoptosis through up-regulating E2F1 in human prostate cancer LNCaP cells", *J. Biol. Chem.*, 2003, 278: 42840-42845.

Narla et al., "KLF6, a candidate tumor suppressor gene mutated in prostate cancer", *Science*, 2001, 294: 2563-2566.

Ng and B. Bonavida, "X-linked inhibitor of apoptosis (XIAP) blocks Apo2 ligand/tumor necrosis factor-related apoptosis-inducing ligand-mediated apoptosis of prostate cancer cells in the presence of mitochondrial activation: sensitization by overexpression of second mitochondria-derived activator of caspase/direct IAP-binding protein with low pl (Smac/DIABLO)", Mol. *Cancer Ther.*, 2002, 1: 1051-1058.

Nomura et al., "The X-linked inhibitor of apoptosis protein inhibits taxol-induced apoptosis in LNCaP cells", *Urol. Res.*, 2003, 31: 37-44.

Otto et al., "E-cadherin: a marker for differentiation and invasiveness in prostatic carcinoma", *Urol. Res.*, 1993, 21: 359-362.

Park et al., "Lovastatin-induced E2F-1 modulation and its effect on prostate cancer cell death", *Carcinogenesis*, 2001, 22: 1727-1731.

Parsons et al., "p63 protein expression is rare in prostate adenocarcinoma: implications for cancer diagnosis and carcinogenesis", *Urology*, 2001, 58: 619-624.

Partin et al., "Combination of prostate-specific antigen, clinical stage, and Gleason score to predict pathological stage of localized prostate cancer. A multi-institutional update.", *JAMA*, 1997, 277: 1445-1451.

Ramaswamy et al., "A molecular signature of metastasis in primary solid tumors", *Nat. Genet.*, 2003, 33: 49-54.

Rhodes et al., "Meta-analysis of microarrays: interstudy validation of gene expression profiles reveals pathway dysregulation in prostate cancer", *Cancer Res.*, 2002, 62: 4427-4433.

Rhodes et al., "Multiplex biomarker approach for determining risk of prostate-specific antigen-defined recurrence of prostate cancer", *J. Natl. Cancer Inst.*, 2003, 95: 661-668.

Rhodes et al., "ONCOMINE: a cancer microarray database and integrated data-mining platform", *Neoplasia*, 2004, 6: 1-6.

Rhodes et al., "Large-scale meta-analysis of cancer microarray data identifies common transcriptional profiles of neoplastic transformation and progression", *Proc. Natl., Acad. Sci., USA*, 2004, 101: 9309-9314.

Rubin et al., "Rapid ("warm") autopsy study for procurement of metastatic prostate cancer", *Clin. Cancer Res.*, 2000, 6: 1038-1045.

Rubin et al., "E-cadherin expression in prostate cancer: a broad survey using high-density tissue microarray technology", *Hum. Pathol.*, 2001, 32: 690-697.

Rubin et al., "alpha-Methylacyl coenzyme A racemase as a tissue biomarker for prostate cancer", *JAMA*, 2002, 287: 1662-1670.

Rubin et al., "Quantitative determination of expression of the prostate cancer protein alpha-methylacyl-CoA racemase using automated quantitative analysis (AQUA): a novel paradigm for automated and continuous biomarker measurements", *Am. J. Pathol.*, 2004, 164: 831-840.

Rubin et al., "Overexpression, amplification, and androgen regulation of TPD52 in prostate cancer", *Cancer Res.*, 2004, 64: 3814-382.

Santagata et al., "JAGGED1 expression is associated with prostate cancer metastasis and recurrence", *Cancer Res.*, 2004, 64: 6854-6857.

Shurbaji et al., "Immunohistochemical detection of a fatty acid synthase (OA-519) as a predictor of progression of prostate cancer", *Hum. Pathol.*, 1996, 27: 917-921.

Signoretti et al., "p63 is a prostate basal cell marker and is required for prostate development", *Am. J. Pathol.*, 2000, 57: 1769-1775.

Singh et al., "Gene expression correlates of clinical prostate cancer behavior", *Cancer Cell*, 2002, 1: 203-209.

Swinnen et al., "Overexpression of fatty acid synthase is an early and common event in the development of prostate cancer", *Int. J. Cancer*, 2002, 98:19-22.

Tsihlias et al., "Loss of cyclin-dependent kinase inhibitor p27Kip1 is a novel prognostic factor in localized human prostate adenocarcinoma", *Cancer Res.*, 1998, 58: 542-548.

Umbas et al., "Expression of the cellular adhesion molecule E-cadherin is reduced or absent in high-grade prostate cancer", *Cancer Res.*, 1992, 52: 5104-5109.

Umbas et al., "Decreased E-cadherin expression is associated with poor prognosis in patients with prostate cancer", *Cancer Res.*, 1994, 54: 3929-3933.

Varambally et al., "The polycomb group protein EZH2 is involved in progression of prostate cancer", *Nature*, 2002, 419: 624-629.

Varambally et al., "Integrative genomic and proteomic analysis of prostate cancer reveals signatures of metastatic progression", *Cancer Cell*, 2005, 8: 393-406.

Wang et al., "PrLZ, a novel prostate-specific and androgen-responsive gene of the TPD52 family, amplified in chromosome 8q21.1 and overexpressed in human prostate cancer", *Cancer Res.*, 2004, 64: 1589-1594.

Welsh et al., "Analysis of gene expression identifies candidate markers and pharmacological targets in prostate cancer", *Cancer Res.*, 2001, 61: 5974-5978.

Xu et al., "Identification of differentially expressed genes in human prostate cancer using subtraction and microarray", *Cancer Res.*, 2000, 60:1677-1682.

Yang et al., "Low p27 expression predicts poor disease-free survival in patients with prostate cancer", *J. Urol.*, 1998, 159: 941-945.

Yu Yan Ping et al., "Gene expression alterations in prostate cancer predicting tumor aggression and preceding development", *J. Clin. Oncol.*, 2004, 22: 2790-2799.

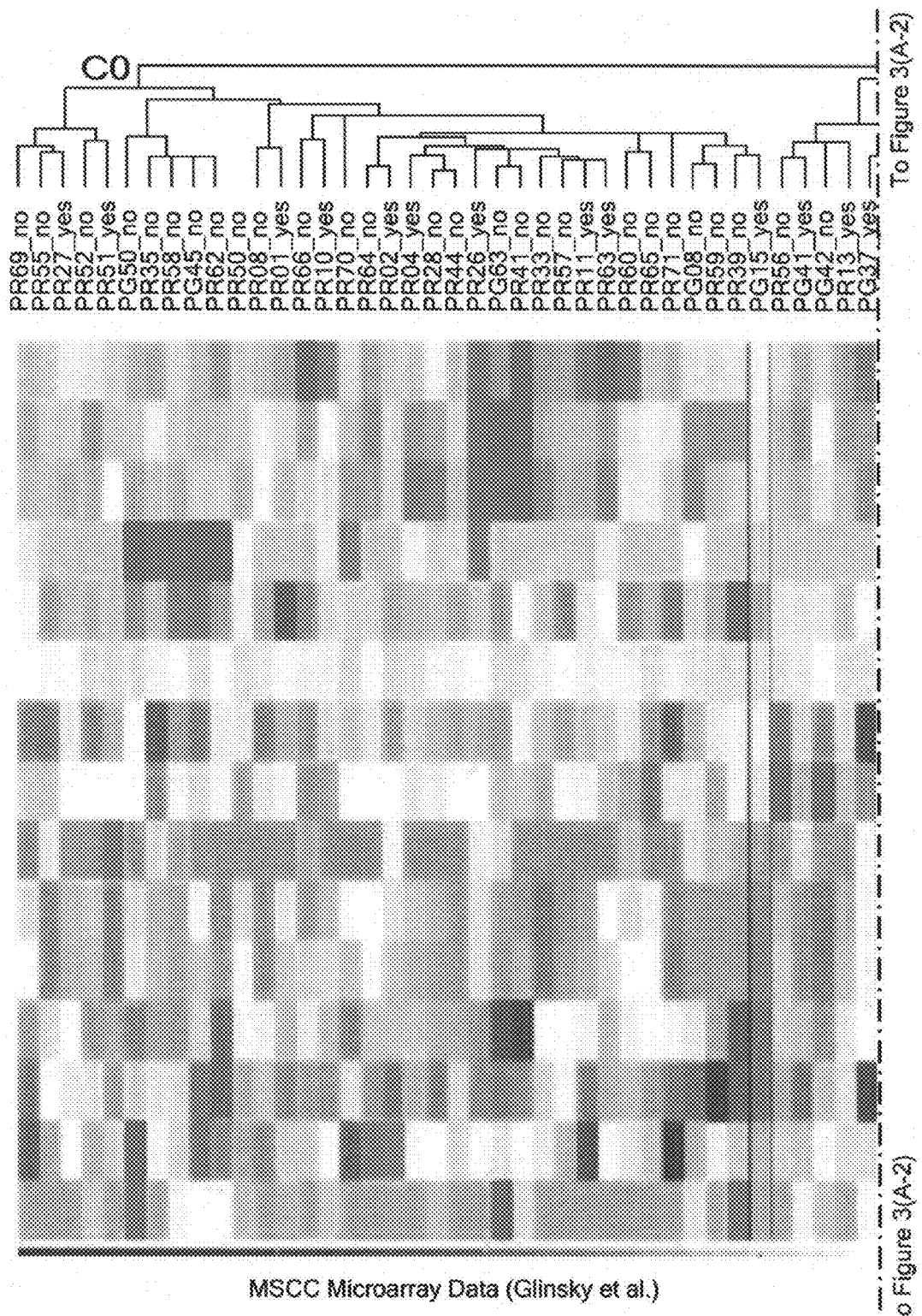
Figure 3(A-1)

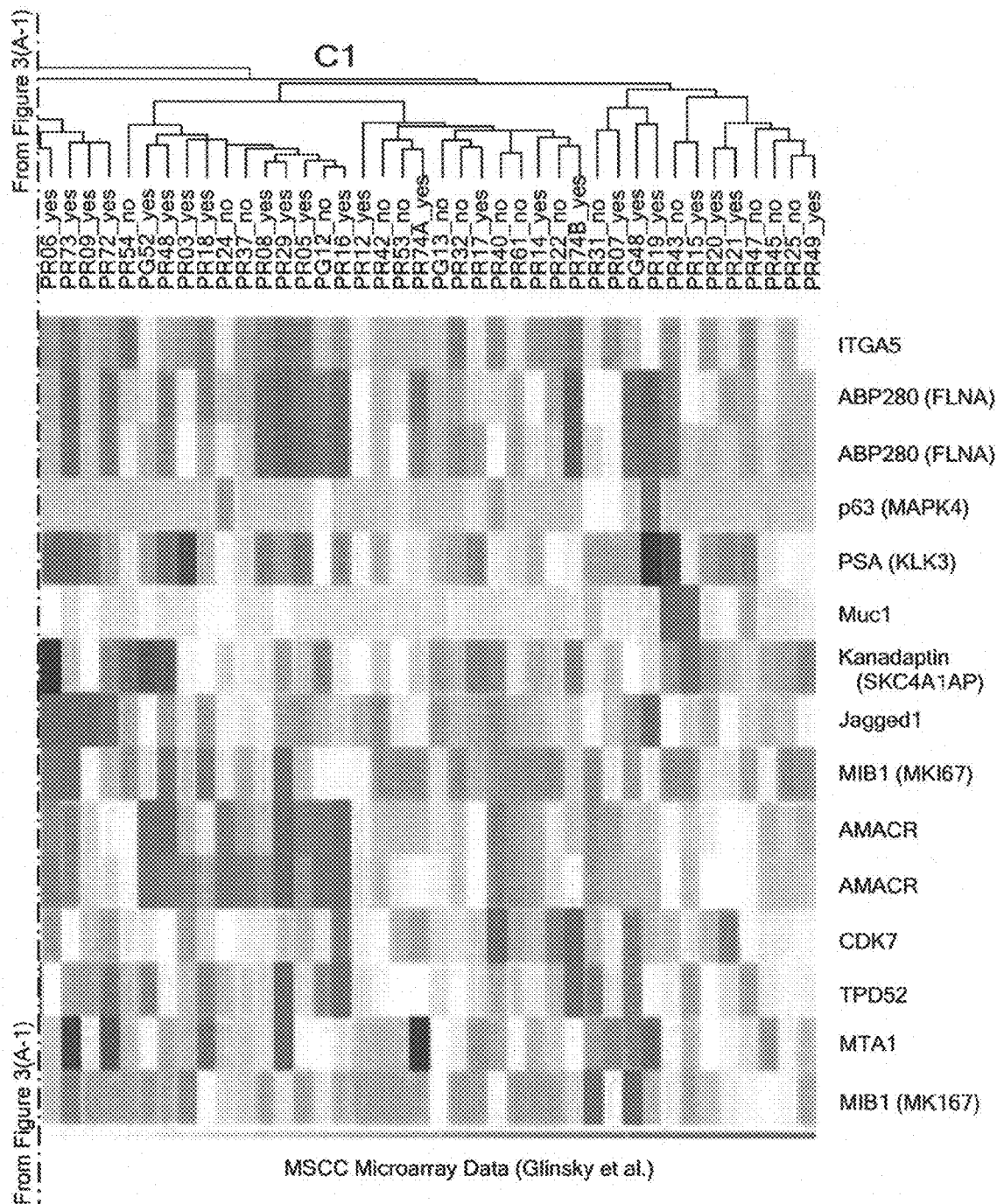
Figure 3(A-2)

|  | BENIGN | | LPCa | | META | | WAP | | SM_CL | |
|---|---|---|---|---|---|---|---|---|---|---|
|  | Mean | CI (95%) | Mean | CI (95%) | Mean | CI (95%) | Mean | CI (95%) | Mean | CI (95%) |
| ABP280 (FLNA) | 0,65 | 0,69 | 0.42 | 1.02 | -1.61 | 0.71 | -0.63 | 1.46 | -0.57 | 0.02 |
| AMACR | -0,87 | 0,22 | 0.76 | 1.05 | -0.20 | 2.05 | 0.64 | 2.82 | -0.36 | 0.32 |
| AR | 0,33 | 1,77 | 0.37 | 1.57 | -0.40 | 1.97 | -0.44 | 2.14 | -1.73 | 1.09 |
| BM28 | -0,63 | 0,44 | 0.11 | 1.41 | 0.07 | 2.98 | 0.54 | 1.90 | 2.27 | 1.64 |
| BUB3 | 0,01 | 0,73 | 0.42 | 1.10 | -0.13 | 2.83 | -0.82 | 3.35 | 0.27 | 1.73 |
| CaMKK | 0,03 | 1,45 | 0.18 | 0.86 | 0.18 | 2.99 | -0.05 | 3.08 | -0.55 | 0.95 |
| CASPASE3 | 1,00 | 0,89 | -0.30 | 1.15 | -0.17 | 1.94 | -1.35 | 0.84 | -1.03 | 0.68 |
| CDK7 | 0,18 | 1,09 | 0.33 | 1.47 | -0.58 | 2.39 | 0.19 | 3.00 | -1.84 | 1.30 |
| DYNAMIN | 0,10 | 1,32 | 0.73 | 1.05 | -0.74 | 1.80 | -0.83 | 2.25 | 0.25 | 2.74 |
| E2F1 | -0,15 | 1,16 | 0.07 | 1.22 | 0.46 | 2.70 | -0.56 | 2.02 | -0.12 | 5.72 |
| E-CADHERIN | -0,03 | 1,33 | 0.31 | 1.48 | -0.66 | 2.00 | 0.64 | 2.13 | -2.42 | 1.93 |
| EXPORTIN | 0,02 | 1,25 | 0.24 | 1.44 | -0.18 | 2.41 | -0.21 | 3.96 | -0.40 | 0.95 |
| EZH2 | -0,46 | 0,83 | 0.08 | 1.31 | 0.00 | 2.24 | 0.45 | 1.76 | 2.77 | 3.89 |
| FAS | -0,28 | 2,00 | 0.08 | 1.58 | 0.22 | 2.54 | 0.47 | 2.40 | -0.49 | 1.15 |
| GAS7 | 0,20 | 1,54 | -0.09 | 1.49 | 0.05 | 2.27 | 0.24 | 2.83 | 0.12 | 3.13 |
| GS28 | 0,18 | 0,84 | 0.28 | 0.91 | 0.34 | 0.53 | -1.00 | 4.36 | -0.53 | 2.19 |
| ICBP90 | -0,42 | 0,98 | 0.58 | 1.86 | -0.47 | 2.30 | -0.46 | 1.23 | 1.95 | 2.58 |
| ITGA5 | 0,15 | 1,14 | 0.18 | 1.25 | -1.34 | 1.31 | 0.31 | 1.42 | -0.40 | 0.43 |
| JAGGED1 | -0,77 | 0,71 | -0.30 | 0.47 | 1.11 | 0.98 | 1.23 | 2.20 | 1.15 | 0.74 |
| JAM1 | -0,03 | 1,16 | 0.06 | 0.85 | -1.24 | 2.43 | 0.75 | 1.37 | 1.56 | 3.48 |
| KANADAPTIN | -0,61 | 1,22 | 0.23 | 1.12 | -0.24 | 1.69 | 1.66 | 1.34 | -1.54 | 1.25 |
| KLF6 | -0,09 | 1,41 | -0.05 | 1.24 | -0.62 | 2.66 | 1.11 | 2.60 | -0.02 | 2.50 |
| KRIP1 | -0,35 | 1,43 | 0.33 | 1.58 | 0.02 | 1.66 | -0.15 | 1.90 | 1.57 | 6.30 |
| LAP2 | -0,10 | 0,90 | -0.02 | 1.14 | -0.71 | 2.75 | 0.92 | 2.39 | 1.18 | 4.18 |
| MCAM | -0,40 | 0,86 | 0.05 | 1.50 | 0.93 | 2.72 | -0.16 | 2.38 | -1.32 | 1.42 |
| MIB1 (MKI67) | -0,49 | 0,11 | -0.17 | 0.52 | -0.36 | 0.44 | 1.21 | 3.31 | 3.05 | 0.79 |
| MTA1 | -0,25 | 1,04 | 0.67 | 0.93 | -0.99 | 2.33 | 0.38 | 2.91 | -0.32 | 2.51 |
| MUC1 | -0,33 | 0,26 | -0.30 | 1.28 | -0.24 | 0.87 | 1.16 | 3.21 | 2.75 | 0.71 |
| MYOSIN-VI | -0,48 | 1,04 | 0.24 | 1.73 | 0.58 | 2.10 | 0.49 | 2.66 | -1.40 | 0.68 |
| P27 | 0,62 | 1,42 | 0.20 | 1.78 | -0.26 | 2.05 | -1.30 | 1.06 | 0.04 | 0.11 |
| P63 | 1,30 | 0,48 | -0.76 | 0.26 | -0.77 | 0.24 | -0.27 | 1.84 | -0.34 | 0.48 |
| PAXILLIN | 0,01 | 1,49 | 0.32 | 2.30 | -0.92 | 0.95 | 0.31 | 2.50 | 0.18 | 1.08 |
| PLCLN | -0,51 | 0,73 | 0.63 | 1.21 | 0.05 | 3.16 | -0.29 | 2.27 | 0.04 | 3.39 |
| PSA(KLK3) | 0,65 | 0,18 | 0.36 | 0.54 | -0.27 | 1.84 | -1.48 | 1.99 | -2.57 | 0.07 |
| RAB27 | 0,79 | 0,50 | 0.30 | 1.44 | -0.95 | 1.78 | -1.16 | 0.64 | -1.62 | 0.27 |
| RBBP | 0,33 | 1,37 | 0.16 | 1.44 | 0.01 | 2.21 | -0.75 | 3.52 | -0.60 | 0.52 |
| RIN1 | 1,00 | 0,54 | 0.35 | 1.36 | -1.16 | 0.51 | -1.13 | 0.46 | -1.11 | 0.25 |
| SAPKalpha | -0,05 | 1,18 | 0.05 | 0.99 | -0.09 | 2.78 | 0.22 | 3.14 | 1.36 | 2.75 |
| TPD52 | -0,11 | 0,71 | -0.04 | 1.35 | 1.22 | 2.42 | -1.05 | 2.44 | 0.05 | 1.32 |
| XIAP | -0,43 | 1,28 | 0.74 | 1.02 | -0.90 | 1.58 | 0.58 | 2.35 | -1.63 | 0.04 |
| ZAG | 0,42 | 1,14 | 0.34 | 2.17 | -0.93 | 1.58 | -0.42 | 1.76 | -1.33 | 0.19 |

Table 1

|  | GROUP | | | | |
|---|---|---|---|---|---|
|  | BENIGN | LPCa | META | WAP | SM_CL |
| ABP280 (FLNA) | 12,05 | 1,74 | -16,81 | -10,88 | -8,60 |
| AMACR | 3,18 | 3,80 | -10,10 | -1,78 | -14,03 |
| CDK7 | 3,39 | 1,51 | -2,94 | -3,56 | -19,28 |
| ITGA5 | -7,43 | 3,77 | -2,73 | 9,44 | 0,27 |
| JAGGED1 | -10,04 | -1,60 | 11,47 | 11,76 | 13,77 |
| KANADAPTIN | -2,57 | 0,49 | 0,00 | 6,20 | -3,41 |
| MIB1 (MKI67) | -6,06 | -4,08 | 5,75 | 8,76 | 32,84 |
| MTA1 | 2,18 | 2,32 | -8,73 | 0,02 | -3,26 |
| MUC1 | -12,92 | 3,43 | 4,59 | 12,31 | 19,73 |
| p63 | 41,51 | -10,06 | -24,94 | -31,61 | -49,72 |
| PSA(KLK3) | 11,82 | 2,26 | -7,45 | -14,78 | -38,07 |
| TPD52 | 2,07 | -4,91 | 6,93 | -3,88 | 12,23 |
| (Constant) | -42,68 | -9,22 | -42,86 | -47,72 | -170,25 |

Table 2

|  | Long-term survivors "Indolent" | Short-term survivors "Unknown" | Cancer death or mets "Lethal" |
|---|---|---|---|
| N | 50 | 105 | 43 |
| Mean age | 69 yr | 77 yr | 72 yr |
| Mean follow-up | 15.4 yr | 5.5 yr | 7.1 yr |
| Stage at dx | | | |
| T1a | 58% | 44% | 19% |
| T1b | 42% | 56% | 81% |
| Gleason, % | | | |
| 4-6 | 80 | 60 | 37 |
| 7 | 18 | 30 | 33 |
| 8-10 | 2 | 10 | 30 |

Figure 6

| 12 Gene Model | |
|---|---|
| | Dysregulated in METS |
| AMACR | - |
| Itga-5 | - |
| ABP280 | - |
| CDK7 | - |
| PSA | - |
| P63 | - |
| MTA1 | - |
| Kanadaptin | - |
| Jagged1 | + |
| MIB1 | + |
| MUC1 | + |
| TPD52 | N/A* |

* antibody did not work.

| 9 Gene Model | |
|---|---|
| | Dysregulated in METS |
| AMACR | - |
| Itga-5 | - |
| Ciap | - |
| Krip1 | - |
| Drbp76 | - |
| Occludin | + |
| Bm28 | + |
| P62 | + |
| Lap2 | + |

Figure 7

|  | N tot/N lethal | Crude Model | Adjusted Model |
|---|---|---|---|
| 12-gene model | | | |
| High risk | 19/9 | 7.7 (2.1-29.0) | 4.3 (1.1-16.8) |
| Mid risk | 151/31 | 2.3 (0.7-7.5) | 1.7 (0.5-5.7) |
| Low risk | 28/3 | REF | REF |
| 9-gene model | | | |
| High risk | 8/4 | 10.8 (2.8-41.6) | 5.1 (1.2-21.3) |
| Mid risk | 156/34 | 2.0 (0.8-5.1) | 1.2 (0.5-3.4) |
| Low risk | 34/5 | REF | REF |
| Combined signature | | | |
| High risk | 19/10 | 17.4 (3.6-83.1) | 8.5 (1.7-42.5) |
| Mid risk | 152/31 | 3.9 (0.9-16.5) | 2.1 (0.5-9.3) |
| Low risk | 27/2 | REF | REF |

Figure 12

| Gene symbol | Gene Name (other aliases) | GenBank Accession Number. | UniGene ID | NCBI locuslink ID |
|---|---|---|---|---|
| ABP280 (FLNA) | filamin A, alpha (actin binding protein 280) (FLN; FMD; MNS; OPD; ABPX; FLN1; NHBP; OPD1; OPD2) | X70082 | Hs.195464 | 2316 |
| AMACR | Alpha-Methylacyl CoA Racemase (RACE) | AF047020 | Hs.508343 | 23600 |
| AR | Androgen Receptor (AIS, NR3C4, SMAX1, HUMARA) | M20132 | Hs.496240 | 367 |
| BM28 | MCM2 minichromosome maintenance deficient 2, mitotin (CCNL1; CDCL1; cdc19; D3S3194; MITOTIN; KIAA0030; MGC10606) | X67334 | Hs.477481 | 4171 |
| BUB3 | BUB3 budding uninhibited by benzimidazoles 3 homolog (BUB3L; hBUB3) | AF053304 | Hs.418533 | 9184 |
| CaMKK | calcium/calmodulin-dependent protein kinase kinase 2, beta (CAMKK2, KIAA0787, CAMKKB, MGC15254) | AF101264 | Hs.297343 | 10645 |
| CASPASE3 | caspase 3, apoptosis-related cysteine peptidase (CASP3, CPP32; SCA-1; CPP32B) | BC016926 | Hs.141125 | 836 |
| CDK7 | cyclin-dependent kinase 7 (cdk7; CG3319; DmCDK7; DmCdk7; DmMO15; Dmcdk7; p40[MO15]) | RefSeq NM_001799 | Dm.2956 | 31441 |
| DYNAMIN | dynamin 1 (DNM, DNM1L, DLP1; DRP1; DVLP; VPS1) | L07807 | Hs.556296 | 10059 |
| E2F1 | E2F transcription factor 1 (RBP3; E2F-1; RBBP3) | RefSeq NM_005225 | Hs.96055 | 1869 |
| E-CADHERIN | cadherin 1, type 1, E-cadherin (epithelial) (CDH1, UVO; CDHE; ECAD; LCAM; Arc-1) | L08599 | Hs.461086 | 999 |
| EXPORTIN | exportin (nuclear export receptor for tRNAs) (XPOT, XPO3) | AF039022 | Hs.85951 | 11260 |
| EZH2 | Enhancer of Zeste 2 (EZH1; ENX-1; MGC9169) | RefSeq NM_004456 | Hs.444082 | 2146 |
| FAS | Fatty Acid Synthase (FASN) | U26644 | Hs.83190 | 2194 |
| GAS7 | growth arrest-specific 7 (KIAA0394, MGC1348) | AB007854 | Hs.462214 | 8522 |
| GS28 | golgi SNAP receptor complex member 1 (GOSR1, GOS28, P28) | AF047438 | Hs.462680 | 9527 |
| ICBP90 | ubiquitin-like, containing PHD and RING finger domains, 1 (UHRF1, Np95, FLJ21925, RNF106; ICBP90) | AF129507 | Hs.108106 | 29128 |
| ITGA5 | integrin, α 5 (fibronectin receptor, α polypeptide) (FNRA; CD49e; VLA5A) | RefSeq NM_002205 | Hs.505654 | 3678 |
| JAGGED1 | jagged 1 (Alagille syndrome) (JAG1, AHD, AWS, HJ1; AGS; AWS; JAGL1) | U61276 | Hs.224012 | 182 |

Table 3 (part 1)

| Gene symbol | Gene Name (other aliases) | GenBank Accession Number | UniGene ID | NCBI locuslink ID |
|---|---|---|---|---|
| JAM1 | F11 receptor (PAM-1, JCAM, JAM-A, JAMA; JAM; KAT) | AF111713 | Hs.517293 | 50848 |
| KANADAPTIN | solute carrier family 4 (anion exchanger), member 1, adaptor protein (SLC4A1AP; HLC3; FLJ10624; MGC120648) | RefSeq NM_018158 | Hs.306000 | 22950 |
| KLF6 | Kruppel-like factor 6 (CPBP, GBF, Zf9, PAC1; BCD1; ST12; COPEB; DKFZp686N0199) | U51869 | Hs.4055 | 1316 |
| KRIP1 | tripartite motif-containing 28 (TRIM28, TIF1B, KAP1, TF1B, RNF96) | RefSeq NM_005762 | Hs.467408 | 10155 |
| LAP2 | erbb2 interacting protein (ERBB2IP, ERBIN) | RefSeq NM_018695 | Hs.519346 | 55914 |
| MCAM | melanoma cell adhesion molecule (MUC18, CD146) | X68264 | Hs.511397 | 4162 |
| MIB1 (MKI67) | antigen identified by monoclonal antibody Ki-67 (KIA; Ki-67) | X65550 | Hs.80976 | 4288 |
| MTA1 | metastasis associated 1 | U35113 | Hs.525629 | 9112 |
| MUC1 | mucin 1, transmembrane (CD227; EMA; PEM; PUM; MAM6; PEMT) | X52229 | Hs.89603 | 4582 |
| MYOSIN-VI | myosin VI (MYO6, KIAA0389; DFNA22; DFNB37; myosin) | RefSeq NM_004999 | Hs.149387 | 4646 |
| P27 | cyclin-dependent kinase inhibitor 1B (CDKN1B, KIP1, P27KIP1, CDKN4) | AF480891 | Hs.238990 | 1027 |
| P63 | tumor protein p73-like (TP73L, KET, p73H, p51, SHFM4, EEC3, p73L) | AB010153 | Hs.137569 | 8626 |
| PAXILLIN | Paxillin (PXN) | U14588 | Hs.446336 | 5829 |
| PLCLN | chloride channel, nucleotide-sensitive, 1A CLNS1A, ICln) | U17899 | Hs.430733 | 1207 |
| PSA | kallikrein 3, (prostate specific antigen) (KLK3; APS; hK3; KLK2A1) | X14810 | Hs.171995 | 354 |
| RAB27 | RAB27A, member RAS oncogene family (GS2; RAM; RAB27; HsT18676; MGC117246) | U38654 | Hs.493512 | 5873 |
| RBBP | | | | |
| RIN1 | Ras and Rab interactor 1 | L36463 | Hs.1030 | 9610 |
| SAPKalpha | mitogen-activated protein kinase 9 (MAPK9; JNK2; JNK2A; JNK2B; PRKM9) | U09759 | Hs.484371 | 5601 |
| TPD52 | tumor protein D52 (D52, hD52, N8L; PC-1; PrLZ) | U18914 | Hs.368433 | 7163 |
| XIAP | X-linked inhibitor of apoptosis (BIRC4BP; XAF1; HSXIAPAF1) | U45880 | Hs.441975 | 54739 |
| ZAG | Zinc alpha-2-glycoprotein (AZGP1; ZA2G) | RefSeq NM_001185 | Hs.546239 | 563 |

Table 3 (part 2)

BIOMARKERS FOR PREDICTING PROSTATE CANCER PROGRESSION

RELATED APPLICATIONS

The present application is a divisional application of U.S. Ser. No. 11/361,517, filed on Feb. 24, 2006, which claims priority to Provisional Application No. 60/656,489 filed on Feb. 25, 2005 and entitled "Biomarkers for Predicting Prostate Cancer Progression", the contents of both of which are incorporated herein by reference in their entirety.

GOVERNMENT SUPPORT

The work described herein was funded by the Specialized Program of Research Excellence for Prostate Cancer (S.P.O.R.E) N.C.I. Grant P50CA90381 (MAR), P50CA69568 (MAR/AMC), N.C.I. grant CA 97063 (AMC, MAR), R01AG21404 (MAR) and the American Cancer Society Grant RSG-02-179-MGO (AMC, MAR).

BACKGROUND OF THE INVENTION

Worldwide, prostate cancer is the third most common cancer and the cause of 6% of cancer deaths in men (M. D. Parkin et al., Eur. J. Cancer, 2001, 37: S4-S66). Its incidence and mortality vary in different parts of the world and are highest in the Western countries (J. M. Chan et al., J. Urol., 2004, 172: S13-S16; K. D. Linton et al., Cancer Treat. Rev., 2003, 29: 151-160). In the U.S., prostate cancer is the most frequently diagnosed and the second leading cause of cancer death in men (A. Jemal et al., Cancer J. Clin., 2003, 53: 5-26). However, despite these high death rates, more men die with prostate cancer than from the disease (J. E. Johansson et al., JAMA, 1997, 277: 467; P. C. Alberstein et al., JAMA, 1998, 280: 975). Since the dilemma in managing patients with prostate cancer is that only a fraction of cases lead to cancer-related death, there is a great need to accurately assess the risk of disease progression in patients with prostate cancer so that appropriate treatment options can be considered.

Several clinical parameters including tumor stage, tumor grade as measured by the Gleason score, and the serum level of prostate-specific antigen (PSA) are typically used to assess the risk of disease progression at the time of diagnosis (A. W. Partin et al., JAMA, 1997, 277: 1445-1451). However, with the adoption of population-based PSA screening, the majority of men in the U.S., who are diagnosed with prostate cancer, are considered at low to intermediate risk for disease-specific mortality while they will often die of co-morbidities. A recent study (R. Etzioni et al., J. Natl. Cancer Inst., 2002, 94: 981-990) has demonstrated that PSA screening may in fact lead to the over-diagnosis and over-treatment of patients with prostate cancer, suggesting that some patients who undergo radical prostatectomy might have lived out their lives without any symptoms of the disease.

Important clinical trials have begun to evaluate watchful-waiting protocols, in which the decision to have surgery is postponed until disease progression is observed, because the risk of waiting as opposed to having immediate surgery is not fully known at the time of initial diagnosis (R. Choo et al., J. Urol., 2002, 167: 1664-1669). One important limitation to current watchful-waiting protocols lies in the subjective criteria used to select patients. If the likelihood of disease progression could be more accurately predicted at diagnosis, the success of such protocols would improve, allowing more men to remain on watchful-waiting protocols for clinically localized disease.

Although surgery may be unnecessary for some patients with clinically localized disease, others will require more aggressive treatment despite having localized disease. After radical prostatectomy, the disease recurs in an estimated 15-30% of patients, suggesting that undetected disease may have spread beyond the prostate gland before surgery (M. Han et al., Urol. Clin. North Am., 2001, 29: 555-565; S. G. Roberts et al., Mayo Clin. Proc., 2001, 76: 576-581). Monograms have been developed that use pretreatment clinical and pathologic parameters to evaluate the likelihood of disease-free survival after radical prostatectomy (M. W. Kattan et al., J. Natl. Cancer Inst., 1998, 90: 766-771) or brachytherapy (M. W. Kattan et al., Urol., 2001, 58: 393-399) for localized prostate cancer. However, these and other models have limitations as demonstrated by good but not excellent associations with outcome (P. L. Ross et al., J. Urol., 2001, 165: 1562-1568).

Given the limitations of current monograms to accurately predict which patients have the greatest risk of developing aggressive prostate cancer, researchers have been focusing on identifying and characterizing biomarkers for prostate diseases. Attempts to explore genetic correlates of tumor behavior have revealed alterations in a number of candidate genes associated with prostate cancer progression, including, for example, loss of p53, amplification of myc, loss of p27, and loss of PTEN. However, no single gene has been shown to have sufficient prognostic utility to warrant clinical implementation.

Recently, genomic methodologies have been used to discover consistent gene expression patterns associated with a given histological or clinical phenotype (T. R. Golub et al., Science, 1999, 286: 531-537; C. M Perou et al., Nature, 2000, 406: 747-752; and L. J. van't Veer et al., Nature, 2002, 415: 530-536). Complementary DNA (cDNA) microarrays have allowed characterization of gene expression profiles for prostate cancer tissue, benign prostate disease tissue, and normal prostate tissue (J. Luo et al., Cancer Res., 2001, 61: 483-4688; J. A. Magee et al., Cancer Res., 2001, 61: 5692-5696; S. M. Dhanasekaran et al., Nature, 2001, 412: 822-826; D. Singh et al., Cancer Cell, 2002, 1: 203-209; J. B. Welsh et al., Cancer Res., 2001, 61: 5974-5978; J. H. Luo et al., Mol. Carcinog., 2002, 33: 25-35).

Although these and other studies have led to the identification of discrete molecular signatures, the development of a robust signature to characterize aggressive prostate cancer has yet to be achieved. There clearly remains a need for improved methods for diagnosing and classifying prostate cancer diseases, and for predicting prostate cancer progression. In particular, systems that would allow physicians to determine which patients might benefit from a more aggressive treatment, and which patients might be spared unnecessary and potentially harmful interventions are highly desirable.

SUMMARY OF THE INVENTION

The present invention relates to the identification and use of gene expression profiles with clinical relevance to prostate diseases. In particular, the invention provides the identity of genes, whose expression, at the transcriptional and protein levels, is correlated with prostate cancer progression. These gene expression profiles may be applied to the diagnosis and/or prognosis of prostate diseases, and are particularly useful in predicting the progression to aggressive and/or metastatic prostate cancer in patients diagnosed with localized prostate cancer. Compared to clinical parameters or biochemical markers used in existing prognosis methods, the expression profiles of the genes disclosed herein constitute a more robust signature of prostate cancer progression and provide a more reliable, non-subjective basis for the selection of appropriate therapeutic regimens. The invention also relates to the screening of drugs that target these genes or their protein products, in particular for the development of therapeutics aimed at modulating prostate cancer progression.

In general, the present invention involves the use of expression levels of a set of genes selected from the group consisting of 41 genes, namely ABP280 (FLNA), AMACR, AR, BM28, BUB3, CaMKK, CASPASE3, CDK7, DYNAMIN, E2F1, E-CADHERIN, EXPORTIN, EZH2, FAS, GAS7, GS28, ICBP90, ITGA5, JAGGED1, JAM1, KANADAPTIN, KLF6, KRIP1, LAP2, MCAM, MIB1 (MKI67), MTA1, MUC1, MYOSIN-VI, P27, P63, PAXILLIN, PLCLN, PSA(KLK3), RAB27, RBBP, RIN1, SAPKalpha, TPD52, XIAP, and ZAG. Preferably, the set of genes comprises 4 or more genes, 5 or more genes, 6 or more genes, 7 or more genes, 8 or more genes, 9 or more genes, 10 or more genes, 11 or more genes, 12 or more genes, or 15 or more genes. More preferably, the set of genes is a 12 gene model consisting of ABP280 (FLNA), AMACR, CDK7, ITGA5, JAGGED1, KANADAPTIN, MIB1 (MKI67), MTA1, MUC1, p63, PSA(KLK3), and TPD52.

More specifically, in one aspect, the present invention provides methods for characterizing prostate tissue in a subject. The methods comprise steps of: providing a sample of prostate tissue obtained from the subject; and determining the levels of expression of a set of genes selected from the 41 genes listed above, to obtain a gene expression pattern for the prostate tissue sample, thereby characterizing the prostate tissue sample. In some embodiments, the set of genes used in these methods is the inventive 12 gene model.

In certain embodiments, determining the levels of expression of the set of genes comprises detecting the expression of mRNA expressed from the genes, for example, by exposing mRNA to a nucleic acid probe complementary to the mRNA. In other embodiments, determining the levels of expression of the set of genes comprises detecting the expression of a polypeptide encoded by the genes, for example, by exposing the polypeptide to an antibody specific to the polypeptide and detecting the binding of the antibody to the polypeptide.

The prostate tissue sample used in the inventive methods may be a fixed, paraffin embedded tissue sample, a fresh tissue sample, or a frozen tissue sample. The prostate tissue sample may be obtained by needle, core or other biopsy.

In certain embodiments, characterizing the prostate tissue further comprises identifying the prostate tissue as benign prostate tissue, localized prostate cancer, hormone naïve metastatic prostate cancer, hormone refractory metastatic prostate cancer, or metastatic small cell prostate cancer, based on the gene expression pattern obtained for the sample.

For example, this may be performed by comparing the gene expression pattern obtained to at least one prostate disease expression profile map, wherein the expression profile map comprises gene expression level information for the set of genes in a particular type of prostate disease; determining the degree of similarity between the gene expression pattern and the expression profile map; and based on the degree of similarity, identifying the prostate tissue. For example, a high degree of similarity between the gene expression pattern obtained and the expression profile map for localized prostate cancer will lead to the identification of the prostate tissue sample as localized prostate cancer.

In another aspect, the present invention provides methods for providing a prognosis to a subject diagnosed with prostate disease. The prognosis methods comprise steps of: providing a sample of prostate tissue obtained from the subject; determining the levels of expression of a set of genes selected from the group of 41 genes listed above, to obtain a gene expression pattern for the sample; and based on the gene expression pattern obtained, providing a prognosis to the subject. Optionally, the methods may further comprise selecting a treatment regimen for the subject, based on the prognosis provided. In some embodiments, the set of genes used in these methods is the 12 gene model disclosed herein.

In certain embodiments, the prognosis is based on the comparison of the gene expression pattern obtained with one or more prostate disease expression profile maps, as described above. Providing a prognosis according to the inventive methods may comprise predicting prostate disease progression, and/or determining the likelihood of developing prostate cancer, aggressive prostate cancer or metastatic prostate cancer, and/or determining a long-term survival outcome.

In another aspect, the present invention provides prostate disease expression profile maps. An expression profile map according to the invention comprises expression level information for a set of genes for a particular type of prostate disease. The set of genes is selected from the 41 genes listed above. In some embodiments, the set of genes is the inventive 12 gene model. In certain embodiments, the prostate disease for which the expression profile map has been established is benign prostate disease, localized prostate cancer, hormone naïve metastatic prostate cancer, hormone refractory metastatic prostate cancer or metastatic small cell prostate cancer. The map may be digital information stored in a computer-readable medium.

In yet another aspect, the present invention provides a prostate disease prognostic portfolio comprising isolated nucleic acid sequences, their complements, or portions thereof, of a set of genes selected from the 41 genes listed above. The nucleic acid sequences, their complements or portions thereof, may be in a matrix suitable for identifying the expression levels of the genes. For example, the matrix may be employed in a microarray, such as a cDNA microarray or an oligonucleotide microarray.

In still another aspect, the present invention provides kits for predicting prostate disease progression in a subject diagnosed with prostate disease. The inventive kits comprise at least one reagent that specifically detects expression levels of a set of genes selected from the 41 genes listed above; and instructions for using the kits for predicting prostate disease progression in a subject. In certain kits, the set of genes is the inventive 12 gene model.

In certain embodiments, the at least one reagent that specifically detects expression levels of the set of genes comprises a nucleic acid probe complementary to mRNA expressed from the genes, for example a cDNA or an oligonucleotide. The nucleic acid probe may or may not be immobilized on a substrate surface. In other embodiments, the at least one reagent comprises an antibody that specifically binds to a polypeptide encoded by the genes. The kits may further comprise one or more of: extraction buffer/reagents and protocol, amplification buffer/reagents and protocol, hybridization buffer/reagents and protocol, immunodetection buffer/reagents and protocol, and labeling buffer/reagents and protocol.

In certain embodiments, the kits further comprise at least one prostate disease expression profile map of the invention for a given set of genes.

In still another aspect, the present invention provides methods for identifying compounds that are potentially useful for modulating prostate disease progression. These methods comprise steps of: providing a prostate cell or cell lysate sample; incubating the cell or cell lysate sample with a candidate compound under certain conditions and for a certain time to obtain a test sample; incubating the cell or cell lysate sample under the same conditions and for the same time absent the candidate compound to obtain a control sample; determining, in the test sample, the levels of expression of a set of genes selected from 41 genes listed above to obtain a gene expression pattern for the test sample; determining, in the control sample, the levels of expression of the same set of genes to obtain a gene expression pattern for the control sample; and identifying the candidate compound as a compound potentially useful to modulate prostate disease progression if the gene expression pattern of the test sample and the gene expression pattern in the control sample are different. In some embodiments, the set of genes used is the inventive 12 gene model.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1 illustrates the protein expression of 41 genes selected for differential expression in prostate cancer progression.

FIG. 3 presents the results of expression array clustering of 80 clinical cases (previously analyzed at Memorial Sloan-Kettering Cancer Center) and Kaplan-Meier Analysis. FIG. 3(A) shows the first hierarchical clustering of the 80 samples using the expression of features representing the 12 genes included in the present model (15 features on U133A). When the 80 cases were clustered using dChip, recurrent and non-recurrent samples were non-randomly distributed between the two major clusters (p<0.01).

Table 1 shows protein expression for the 41 genes represented by mean staining intensity scores and 95% confidence intervals for 5 groups of prostate diseases (benign prostate disease, localized prostate cancer, hormone naïve metastatic prostate cancer, hormone refractory metastatic prostate cancer, and metastatic small cell prostate cancer).

Table 2 shows the Fisher linear discriminant function coefficient (classification model) obtained for the 12 genes.

FIG. 6 shows the characteristics of the Örebro Watchful Waiting Cohort (1977-2005).

FIG. 7 presents two tables that show the genes that were dysregulated in metastatic prostate cancer (METS) samples in the 12-gene model and in the 9-gene model.

Figure 8:
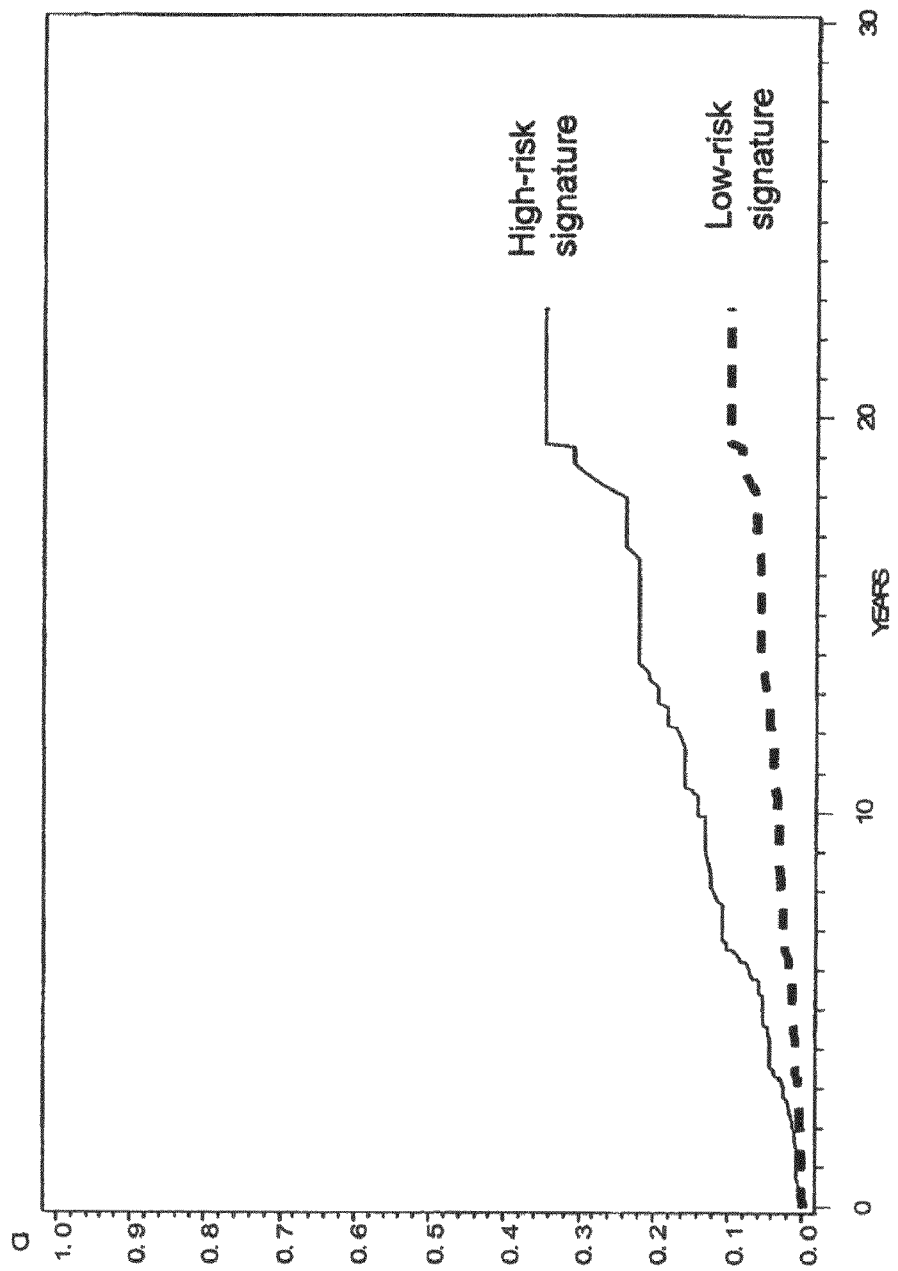

FIG. 8 is a graph showing the cumulative incidence of prostate cancer death or metastasis by the 12-gene model for Gleason 2-6 samples.

Figure 9:
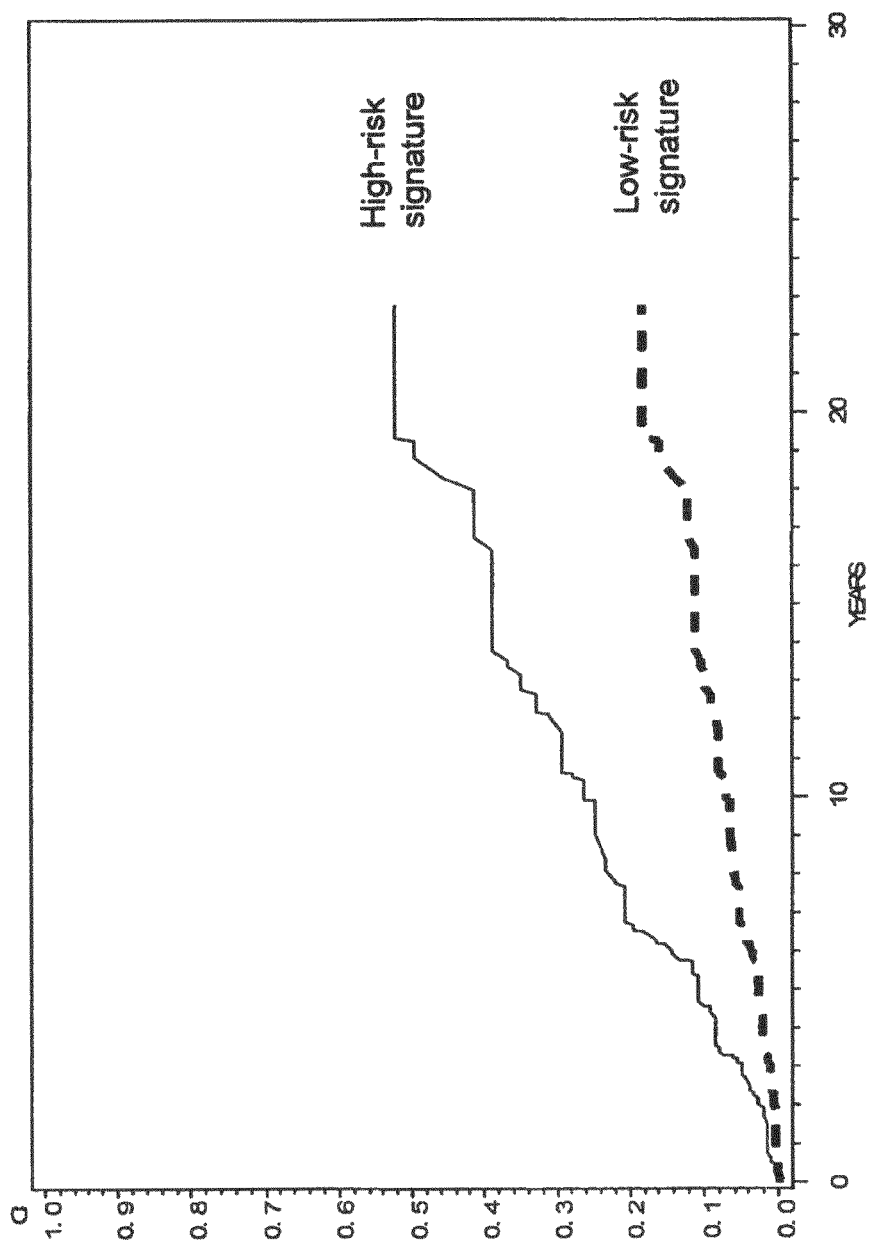

FIG. 9 is a graph showing the cumulative incidence of prostate cancer death or metastasis by the 12-gene model for Gleason 7 samples.

Figure 10:
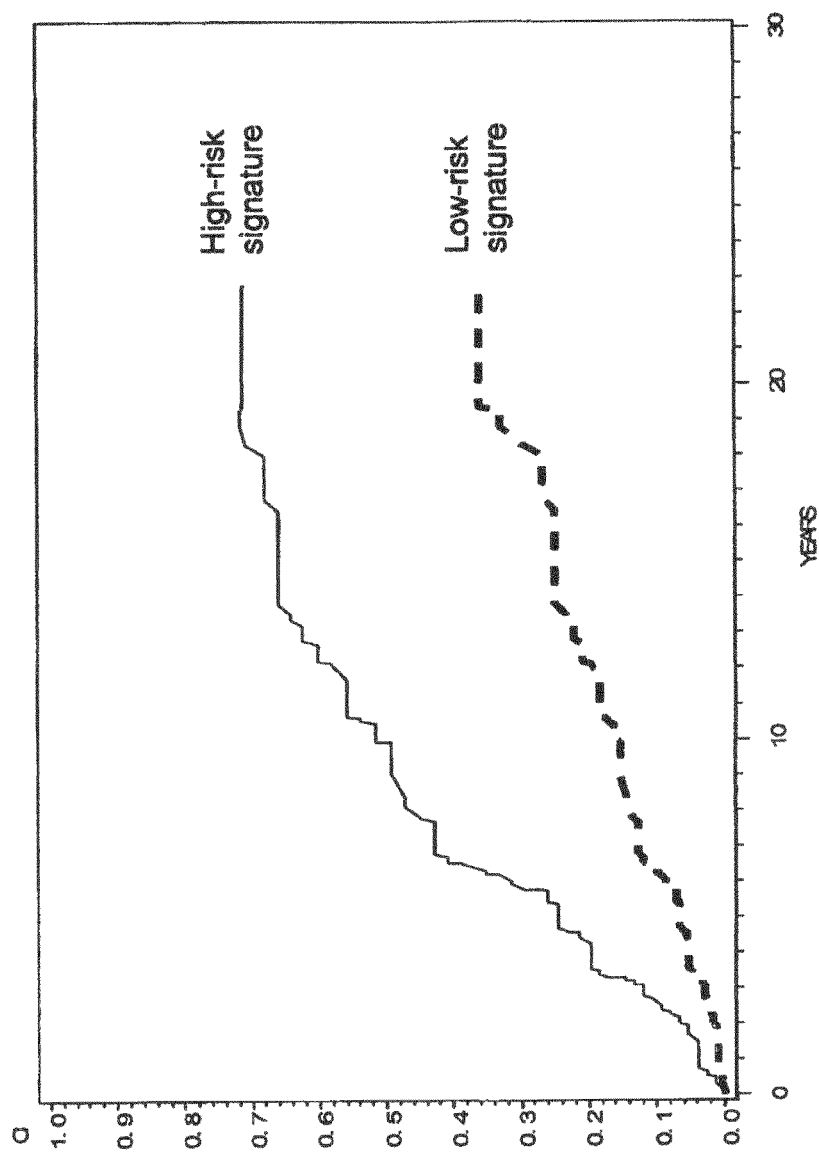

FIG. 10 is a graph showing the cumulative incidence of prostate cancer death or metastasis by the 12-gene model for Gleason 8-10 samples.

Figure 11A:
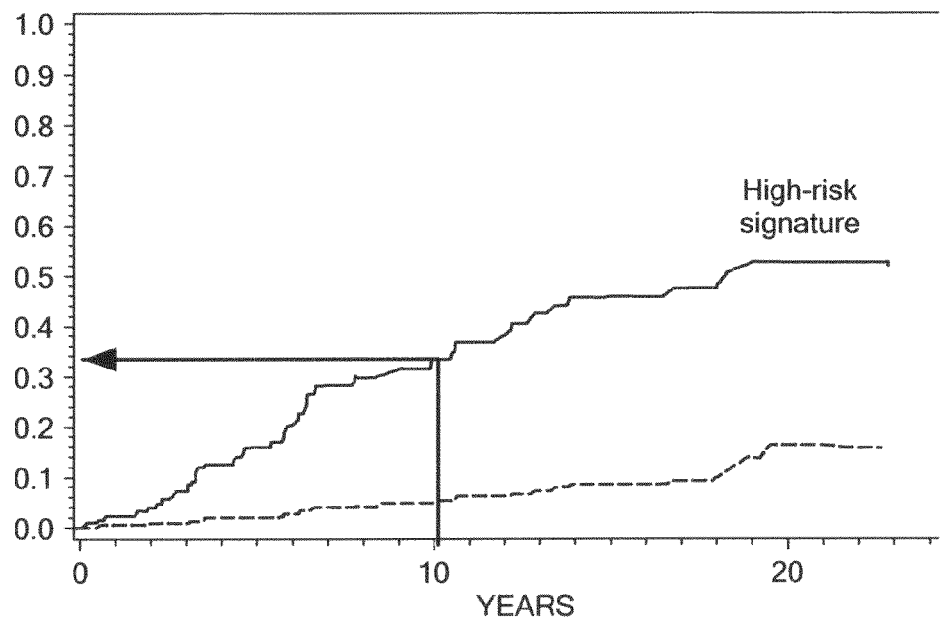
Figure 11B:
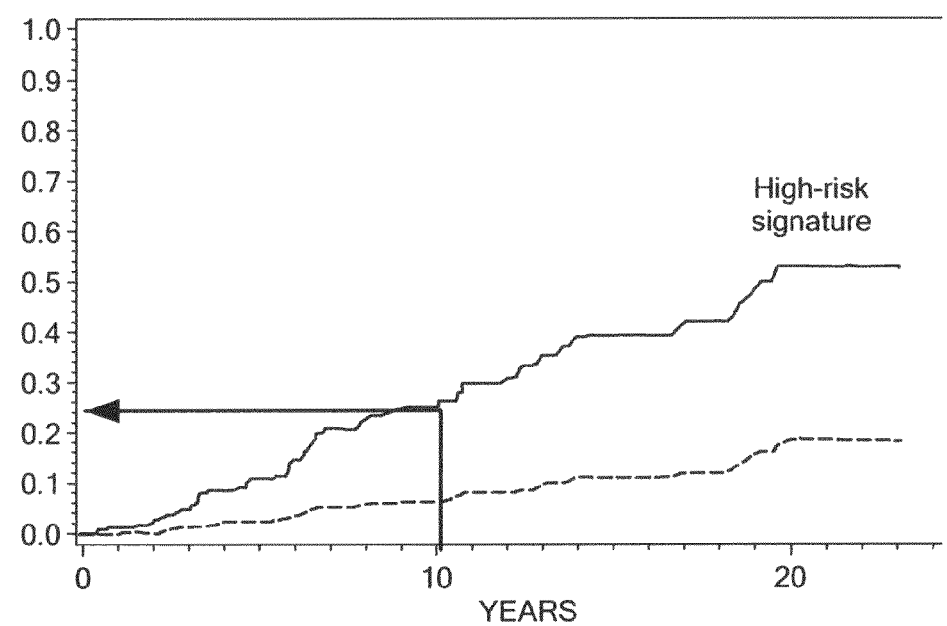

FIG. 11 presents two graphs showing the cumulative incidence of prostate cancer death or metastasis by (A) the combined gene model and (B) the 12-gene model, for Gleason 7 samples.

FIG. 12 shows results of the validation of the 12-gene model, 9-gene model and combined signature.

Table 3 presents the 41 genes along with their names, aliases, and database identifiers.

DEFINITIONS

Throughout the specification, several terms are employed that are defined in the following paragraphs.

As used herein, the term "subject" refers to a male human or another male mammal, that can be afflicted by a prostate disease, including prostate cancer, but may or may not have such a disease. Typically, the terms "subject" and "patient" are used herein interchangeably in reference to a human individual.

As used herein, the term "subject suspected of having prostate cancer" refers to a subject that presents one or more symptoms indicative of prostate cancer or that is being screened for prostate cancer (e.g., during a routine physical examination). A subject suspected of having prostate cancer may also have one or more risk factors. The term encompasses individuals who have not been tested for prostate cancer, individuals who have received an initial diagnosis (e.g., a CT scan showing a mass) but for whom the stage of cancer is not known, as well as individuals for whom the stage and/or grade of cancer has been determined by a conventional method (e.g., Gleason score). The term also includes patients who have previously undergone therapy for prostate cancer, including radical prostatectomy and brachytherapy.

As used herein, the term "subject at risk for prostate cancer" refers to a subject with one or more risk factors for developing prostate cancer. Risk factors include, but are not limited to, gender, age, genetic predisposition, previous incidents with cancer, and pre-existing non-cancer diseases.

As used herein, the term "subject diagnosed with prostate disease" refers to a subject who has been tested and found to have prostate disease. The diagnosis may be performed using any suitable method, including, but not limited to, biopsy, x-ray, blood test, and the methods of the present invention.

As used herein, the term "initial diagnosis" refers to results of initial cancer diagnosis (e.g., the presence or absence of cancerous cells). An initial diagnosis does not include information about the stage of prostate cancer or the prognosis.

The term "providing a prognosis" is used herein to mean providing information regarding the impact of the presence of prostate cancer (e.g., as determined by the methods of the present invention) on a subject's future health. Providing a prognosis may include predicting one or more of: prostate cancer progression, the likelihood of prostate cancer-attributable death, the average life expectancy of the patient, the likelihood that the patient will survive for a given amount of time (e.g., 6 months, 1 year, 5 years, etc), the likelihood that the patient will be disease-free for a specified prolonged period of time, the likelihood of getting prostate cancer, the likelihood of developing aggressive prostate cancer, the likelihood of recurrence, and the risk of metastasis. In certain embodiments, the prognosis methods of the invention are used clinically to make treatment decisions by choosing the most appropriate treatment modalities for any particular patient.

The term "prostate tissue sample" is taken broadly to include a sample of prostate tissue or fluid, as well as cells (or their progeny) isolated from such tissue or fluid. Prostate tissue samples may be tissue or fluid collected from a subject, sections of tissue such as biopsy and autopsy samples, frozen sections taken for histology purposes, and archival tissues with known treatment and/or outcome history. Prostate tissue samples may be collected by any non-invasive means, including, but not limited to, fine needle aspiration and needle biopsy, or, alternatively, by an invasive method, including, but not limited to, surgical biopsy. The term "prostate tissue sample" also includes any material derived by processing a sample of prostate tissue, fluid or cell. Derived material may include, for example, nucleic acid molecules or proteins extracted from the sample.

As used herein, the term "characterizing prostate tissue in a subject" refers to the identification of one or more properties of a prostate tissue sample including, but not limited to, the presence of benign prostate tissue, the presence of cancerous tissue, the presence of pre-cancerous tissue that is likely to become cancerous, the presence of cancerous tissue that is likely to metastasize. In certain embodiments, the prostate tissue is characterized by determination of the expression levels of a set of genes selected from the 41 genes disclosed herein.

As used herein, the term "gene" refers to a polynucleotide that encodes a discrete macromolecular product, be it RNA or a protein, and may include regulatory sequences preceding (5' non-coding sequences) and following (3' non-encoding sequences) the coding sequence. As more than one polynucleotide may encode a discrete product, the term also includes alleles and polymorphisms of a gene that encode the same product, or a functionally associated (including gain, loss, or modulation of function) analog thereof.

The term "gene expression" refers to the process by which RNA and proteins are made from the instructions encoded in genes. Gene expression include transcription and/or translation of nucleic acid material.

The terms "gene expression pattern" and "gene expression profile" are used herein interchangeably. They refer to the expression of an individual gene or of a set of genes. A gene expression pattern may include information regarding the presence of target transcripts in a sample, and the relative or absolute abundance levels of target transcripts.

The term "differentially expressed gene" refers to a gene whose level of expression is different in a subject (or a population of subjects) afflicted with a prostate disease relative to its level of expression in a healthy or control subject (or a population of healthy or control subjects). The term also includes a gene whose level of expression is different at different stages of a prostate disease (e.g., localized prostate cancer vs. metastatic prostate cancer). As will be appreciated by those skilled in the art, a gene may be differentially expressed at the nucleic acid level and/or protein level, or may undergo alternative splicing resulting in a different polypeptide product. Differential expression includes quantitative, as well as qualitative, differences in the temporal or cellular expression pattern in a gene or its expression products. As described in greater details below, a differentially expressed gene, alone or in combination with other differentially expressed genes, is useful in a variety of different applications in diagnostic, therapeutic, prognosis, drug development and related areas. The expression patterns of the differentially expressed genes disclosed herein can be described as a fingerprint or a signature of prostate cancer progression. They can be used as a point of reference to compare and characterize unknown samples and samples for which further information is sought.

The term "RNA transcript" refers to the product resulting from transcription of a DNA sequence. When the RNA transcript is the original, unmodified product of a RNA polymerase catalyzed transcription, it is referred to as the primary transcript. An RNA transcript that has been processed (e.g., spliced, etc) will differ in sequence from the primary transcript. A processed RNA transcript that is translated into protein is often called a messenger RNA (mRNA). The term "messenger RNA or mRNA" refers to a form of RNA that serves as a template to direct protein biosynthesis. Typically, the amount of any particular type of mRNA (i.e., having the same sequence, and originating from the same gene) reflects the extent to which a gene has been expressed.

The term "complementary DNA or cDNA" refers to a DNA molecule that is complementary to mRNA. cDNA can be made by DNA polymerase (e.g., reverse transcriptase) or by directed chemical synthesis.

The term "complementary" refers to nucleic acid sequences that base-pair according to the standard Watson-Crick complementary rules, or that are capable of hybridizing to a particular nucleic acid segment under relatively stringent conditions. Nucleic acid polymers are optionally complementary across only portions of their entire sequences.

The term "hybridizing" refers to the binding of two single stranded nucleic acids via complementary base pairing. The terms "specific hybridization" and "specific binding" are used herein interchangeably. They refer to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular genetic probe and to a lesser extent or not at all, to other genetic probes, for example, when these genetic probes are immobilized on an array.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation. The term "gene expression array" refers to an array comprising a plurality of genetic probes immobilized on a substrate surface that can be used for quantitation of mRNA expression levels. The term "genetic probe", as used herein, refers to a nucleic acid molecule of known sequence, which has its origin in a defined region of the genome and can be a short DNA sequence (i.e., an oligonucleotide), a PCR product, or mRNA isolate. Genetic probes are gene-specific DNA sequences to which nucleic acid fragments from a test sample are hybridized. Genetic probes specifically bind to nucleic acid of complementary or substantially complementary sequence through one or more types of chemical bonds, usually through hydrogen bond formation.

As used herein, the term "a reagent that specifically detects expression levels" refers to one or more reagents used to detect the expression of one or more genes (e.g., a gene selected from the 41 genes provided herein). Examples of suitable reagents include, but are not limited to, nucleic acid probes capable of specifically hybridizing to the gene of interest, PCR primers capable of specifically amplifying the gene of interest, and antibodies capable of specifically binding to proteins expressed by the gene of interest. The term "amplify" is used in the broad sense to mean creating an amplification product. "Amplification", as used herein, generally refers to the process of producing multiple copies of a desired sequence, particularly those of a sample. A "copy" does not necessarily mean perfect sequence complementarity or identity to the template sequence.

The term "prostate disease expression profile map" refers to a presentation of expression levels of a set of genes in a particular type of prostate tissue (e.g., benign prostate tissue, localized prostate cancer, hormone naïve metastatic prostate cancer, hormone refractory metastatic prostate cancer, or metastatic small cell prostate cancer). The map may be presented as a graphical representation (e.g., on paper or a computer screen), a physical representation (e.g., a gel or array) or a digital representation stored in a computer-readable medium. Each map corresponds to a particular type of prostate tissue, and thus provides a template for comparison to a patient sample. In preferred embodiments, maps are generated from pooled samples comprising tissue samples from a plurality of patients with the same type of prostate tissue.

As used herein, the term "modulation of prostate cancer progression" refers to the ability of a compound to increase or decrease the likelihood that a prostate cancer will progress to an aggressive prostate cancer and/or will metastasize. Generally, compounds therapeutically useful are those that decrease the likelihood of prostate cancer progression.

The term "computer readable medium" refers to any device or system for storing or providing information (e.g., data and instructions) to a computer processor. Examples of computer readable media include, but are not limited to, DVDs, CDs, hard disk drives, magnetic tape and servers for streaming media over networks.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

DETAILED DESCRIPTION OF CERTAIN PREFERRED EMBODIMENTS

As mentioned above, the present invention provides improved systems and strategies for predicting prostate cancer progression. In particular, the present invention provides the identity of 41 genes whose expression, at the transcriptional and protein levels, has been found to correlate with prostate cancer progression. As detailed in the Examples Section, these 41 genes were selected from a group of genes that were identified through a selection process which sorted through over 1383 genes by evaluating a combination of cDNA expression array analysis and a high throughput proteomic screen (S. Varambally et al., "Integrative genomic and proteomic analysis of prostate cancer reveals signatures of metastatic progression", Cancer Cell, 2005, 8: 393-406; T. A. Bismar et al., "Defining Aggressive Prostate Cancer Using a 12 Gene Model", Neoplasia, January 2006, accepted for publication; each of which is incorporated by reference in its entirety).

The 41 genes provided by the present invention include ABP280 (FLNA), AMACR, AR, BM28, BUB3, CaMKK, CASPASE3, CDK7, DYNAMIN, E2F1, E-CADHERIN, EXPORTIN, EZH2, FAS, GAS7, GS28, ICBP90, ITGA5, JAGGED1, JAM1, KANADAPTIN, KLF6, KRIP1, LAP2, MCAM, MIB1 (MKI67), MTA1, MUC1, MYOSIN-VI, P27, P63, PAXILLIN, PLCLN, PSA(KLK3), RAB27, RBBP, RIN1, SAPKalpha, TPD52, XIAP, and ZAG. These genes, their aliases and database identifiers are presented in Table 3.

The present invention also encompasses the recognition that robust predictive models containing limited numbers of genes may be identified from the 41 genes listed above. These models or sets of genes can be used for performing relatively low cost prostate disease diagnosis and prediction of prostate cancer progression. Accordingly, in one aspect, the present invention provides for the identification, generation, and use of expression profiles of sets of genes selected from the 41 genes disclosed herein.

Identification of Sets of Genes

The methods of the present invention may be practiced using any set of genes selected from the 41 genes disclosed herein, as long as the expression profiles of the genes within a given set discriminate between prostate disease progression outcomes (for example between localized prostate cancer unlikely to become aggressive and/or to metastasize and localized prostate cancer likely to become aggressive and/or to metastasize).

The identification of such sets of genes may be performed by any suitable selection method, including, but not limited to, cluster analysis, supported vector machines, neural networks or other algorithms. A set of genes identified by such selection methods is generally capable of predicting the classification of an unknown sample based on the expression levels of genes used for the discrimination. "Leave one out" cross-validation may be used to test the performance of various models and to help identify weights (genes) that are uninformative (e.g., redundant) or detrimental to the predictive ability of the gene model.

For example, gene models can be tested by using expression array data sets that have associated clinical outcomes. One limitation of this approach is that the development of a clinical tissue-based test requires using antibodies against proteins that can be assessed in biopsy samples. A preferred strategy to the identification of predictive sets of genes is described in the Examples section. This approach includes measuring in situ expression of the proteins using a prostate cancer progression tissue microarray (TMA).

Tissue arrays may be constructed according to a variety of techniques. According to one procedure, a commercially available mechanical device (e.g., the manual tissue arrayer MTA1 from Beecher Instruments of Sun Prairie, Wis.) is used to remove a 0.6-μ-diameter, full thickness "core" from a paraffin block (the donor block) prepared from each patient, and insert the core into a separate paraffin block (the recipient block) in a designated location on a grid. Cores from as many as about 400 patients can be inserted into a single recipient block. The resulting tissue array may be processed into thin sections for gene selection procedures.

Preferred sets of genes of the present invention are sets identified by measuring in situ expression of the proteins using a prostate cancer progression tissue microarray. One preferred set of genes is the 12 gene model described in the Examples section, which consists of ABP280 (FLNA), AMACR, CDK7, ITGA5, JAGGED1, KANADAPTIN, MIB1 (MKI67), MTA1, MUC1, p63, PSA(KLK3), and TPD52.

Sets of genes useful in the practice of the methods of the present invention generally comprise limited numbers of genes, for example, 4 or more genes, 5 or more genes, 6 or more genes, 7 or more genes, 8 or more genes, 9 or more genes, 10 or more genes, 11 or more genes, 12 or more genes, or 15 or more genes. As will be appreciated by those skilled in the art, gene models with even a small set of reference gene expression data may exhibit high discriminative power and therefore may be highly useful and accurate to predict the status of an unknown prostate tissue sample.

Prostate Disease Portfolios And Prostate Disease Expression Profile Maps

The sets of genes whose expression profiles best correlate with prostate cancer progression make up the prostate disease prognostic portfolios of the invention. More specifically, a prostate disease prognostic portfolio according to the present invention comprises isolated nucleic acid sequences, their complements or portions thereof, of a set of genes capable of discriminating between prostate disease progression outcomes. In certain embodiments, the isolated nucleic acid sequences, their complements or portions thereof, are in a matrix, which is preferably suitable for determining the expression levels of the genes contained therein. For example, the matrix is employed in a microarray.

Information on expression levels of a given set of genes obtained for a particular type of prostate disease (preferably, from a large number of patients afflicted with the same prostate disease) may be grouped to form a prostate disease expression profile map. Each expression profile map provides a template for comparison to gene expression patterns generated from unknown prostate tissue samples. Prostate disease expression profile maps may be presented as a graphical representation (e.g., on paper or a computer screen), a physical representation (e.g., a gel or array) or a digital representation stored in a computer-readable.

As will be appreciated by those of ordinary skill in the art, sets of genes whose expression profiles correlate with prostate cancer progression, and which can discriminate between prostate disease progression outcomes, may be used to identify/study unknown prostate tissue samples. Accordingly, the present invention provides methods for characterizing prostate tissue in a subject suspected of having prostate cancer, diagnosed with prostate cancer or at risk for prostate cancer.

Determination of Gene Expression Levels

The diagnostic/prognostic methods of the present invention generally involve the determination of expression levels of a set of genes in a prostate tissue sample. Determination of gene expression levels in the practice of the inventive methods may be performed by any suitable method. For example, determination of gene expression levels may be performed by detecting the expression of mRNA expressed from the genes of interest and/or by detecting the expression of a polypeptide encoded by the genes.

Any suitable method can be used, including, but not limited to, Southern blot analysis, Northern blot analysis, polymerase chain reaction (PCR) (see, for example, U.S. Pat. Nos. 4,683, 195; 4,683,202, and 6,040,166; "*PCR Protocols: A Guide to Methods and Applications*", Innis et al. (Eds), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, etc.

Other useful methods include, but are not limited to, any immunohistochemistry (ICH) based, antibody (including auto-antibodies against the protein) based, mass spectrometry based, and image (including use of labeled ligand) based methods known in the art for the detection of proteins. Other suitable methods include proteomics-based methods. Proteomics includes, among other things, study of the global changes of protein expression in a sample. Proteomics typically includes the following steps: (1) separation of individual proteins in a sample by 2-D electrophoresis (2-D PAGE), (2) identification of individual proteins recovered from the gel (e.g., by mass spectrometry or N-terminal sequencing), and (3) analysis of the data using bioinformatics.

Alternatively, gene expression levels may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Prostate Tissue Samples

The methods of the invention may be applied to the study of any prostate tissue sample, i.e., a sample of prostate tissue or fluid, as well as cells (or their progeny) isolated from such tissue or fluid. Prostate tissue samples may be fresh or frozen samples collected from a subject, or archival tissue samples, for example, with known diagnosis, treatment and/or outcome history. Prostate tissue may be collected by any non-invasive means, such as, for example, fine needle aspiration and needle biopsy, or alternatively, by an invasive method, including, for example, surgical biopsy.

The inventive methods may be performed at the single cell level (e.g., isolation of cancerous cells from the prostate tissue sample). However, preferably, the inventive methods are performed using a sample comprising many cells, where the assay is "averaging" expression over the entire collection of cells and tissue present in the sample. Preferably, there is enough of the prostate tissue sample to accurately and reliably determine the expression levels of the set of genes of interest. In certain embodiments, multiple samples may be taken from the same prostate tissue in order to obtain a representative sampling of the tissue.

In certain embodiments, RNA is extracted from the prostate tissue sample before analysis. Methods of RNA extraction are well known in the art (see, for example, J. Sambrook et al., "*Molecular Cloning: A Laboratory Manual*", 1989, 2$^{nd}$ Ed., Cold Spring Harbour Laboratory Press: New York). Most methods of RNA isolation from bodily fluids or tissues are based on the disruption of the tissue in the presence of protein denaturants to quickly and effectively inactivate RNases. Generally, RNA isolation reagents comprise, among other components, guanidinium thiocyanate and/or beta-mercaptoethanol, which are known to act as RNase inhibitors. Isolated total RNA is then further purified from the protein contaminants and concentrated by selective ethanol precipitations, phenol/chloroform extractions followed by isopropanol precipitation (see, for example, P. Chomczynski and N. Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from bodily fluids or tissues (e.g., prostate tissue samples) and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Giagen, Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "*Molecular Cloning: A Laboratory Manual*", 1989, 2$^{nd}$ Ed., Cold Spring Harbour Laboratory Press: New York; "*Short Protocols in Molecular Biology*", F. M. Ausubel (Ed.), 2002, 5$^{th}$ Ed., John Wiley & Sons; U.S. Pat. Nos. 4,683,195; 4,683, 202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In certain embodiments, the RNA isolated from the prostate tissue sample (for example, after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). Preferably, the detectable agent is selected such that it generates a signal which can be measured and whose intensity is related to the amount of labeled nucleic acids present in the sample being analyzed. In array-based analysis methods, the detectable agent is also preferably selected such that it generates a localized signal, thereby allowing spatial resolution of the signal from each spot on the array.

Methods for labeling nucleic acid molecules are well-known in the art. For a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachment of fluorescent dyes (see, for example, L. M. Smith et al., Nucl. Acids Res. 1985, 13: 2399-2412) or of enzymes (see, for example, B. A. Connoly and P. Rider, Nucl. Acids. Res. 1985, 13: 4485-4502); chemical modifications of nucleic acid fragments making them detectable immunochemically or by other affinity reactions (see, for example, T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

However, as mentioned above, in some embodiments, the expression levels are determined by detecting the expression of a gene product (e.g., protein) thereby eliminating the need to obtain a genetic sample (e.g., RNA) from the prostate tissue sample.

Characterization of Prostate Tissue and Prediction of Prostate Cancer Progression The inventive sets of genes or gene models with high discriminative power may be used to characterize unknown prostate tissue samples and/or to predict prostate cancer progression in a subject.

In order to characterize prostate tissue in a subject, or to predict prostate cancer progression in a subject, the expression levels of the set of genes of interest are determined for a sample of prostate tissue obtained from the subject and compared to the expression levels in reference samples. Reference samples may be obtained from healthy individuals and from individuals afflicted with a given type of prostate disease (e.g., benign prostate disease, localized prostate cancer, hormone naïve metastatic prostate cancer, hormone regulatory mestastatic prostate cancer, and metastatic small cell prostate cancer). As mentioned above, reference expression levels of the set of genes of interest are preferably determined from a significant number of individuals afflicted with the same prostate disease (e.g., with known treatment and outcome history), and an average or mean is obtained. In certain preferred embodiments, the gene expression levels determined for the prostate tissue sample obtained from the subject are compared to at least one prostate disease expression profile map, as described above.

Comparison of gene expression levels according to the methods of the present invention is preferably performed after the gene expression levels obtained have been corrected for both differences in the amount of sample assayed and variability in the quality of the sample used (e.g., amount and quality of mRNA tested). Correction may be carried out by normalizing the levels against reference genes in the same sample. Typically, "housekeeping genes", such as actin, GAPDH, HPRT, CPB, and G6PD, are used for this normalization. Alternatively or additionally, normalization can be based on the mean or median signal (e.g., Ct in the case of RT-PCR) of all assayed genes or a large subset thereof (global normalization approach).

For a given set of genes, comparison of a gene expression pattern obtained for a prostate tissue sample against an expression profile map established for a particular type of prostate disease may comprise comparison of the normalized expression levels on a gene-by-gene basis and/or comparison of ratios of expression levels within the set of genes. In addition, the gene expression pattern obtained for the prostate tissue sample being analyzed may be compared against each of the prostate disease expression profile maps or against a gene expression profile that defines delineations made based upon all the prostate disease expression profile maps.

Selection of Appropriate Treatment

Using the methods described herein, skilled physicians may select and prescribe treatments adapted to each individual patient based on the prognosis provided to the patient through determination of the expression levels of a gene model. In particular, since methods disclosed herein allow for discrimination between non-aggressive localized prostate cancer unlikely to become aggressive and non-aggressive localized prostate cancer likely to become aggressive and/or to metastasize, these methods provide physicians with a non-subjective means to determine which patients may benefit from a more aggressive treatment, and which patients may be spared unnecessary interventions.

Selection of an appropriate therapeutic regimen for a given patient may be made based solely on the prognosis provided by the inventive methods. Alternatively, the physician may also consider other clinical or pathological parameters and/or biochemical factors used in existing methods to assess the risk of disease progression, including tumor stage, tumor grade (e.g., as measured by the Gleason score), and the serum level of prostate-specific antigen (PSA).

Kits

In another aspect, the present invention provides kits comprising materials useful for carrying out the methods of the invention. The diagnostic/prognosis procedures described herein may be performed by diagnostic laboratories, experimental laboratories, or practitioners. The invention provides kits which can be used in these different settings.

Basic materials and reagents required for characterizing prostate tissue, diagnosing prostate disease in a subject, and/or predicting prostate cancer progression in a subject according to methods of the present invention may be assembled together in a kit. In certain embodiments, the kit comprises at least one reagent that specifically detects expression levels of a set of genes selected from the 41 genes disclosed herein, and instructions for using the kit according to one or more methods of the invention. Each kit necessarily comprises reagents which render the procedure specific. Thus, for detecting mRNA expressed by at least one gene of the set, the reagent will comprise a nucleic acid probe complementary to mRNA, such as, for example, a cDNA or an oligonucleotide. The nucleic acid probe may or may not be immobilized on a substrate surface (e.g., a microarray). For detecting a polypeptide product encoded by at least one gene of the set, the reagent will comprise an antibody that specifically binds to the polypeptide.

Depending on the procedure, the kit may further comprise one or more of: extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may also be included in the kit.

Reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps for the disclosed methods may also be provided. The individual containers of the kit are preferably maintained in close confinement for commercial sale.

In certain embodiments, the kits of the present invention further comprise control samples. For example, a kit may include samples of total mRNA derived from tissue of various physiological states, such as, for example, normal prostate tissue, benign prostate tissue, localized prostate tissue, and metastatic prostate tissue, to be used as controls. In other embodiments, the inventive kits comprise at least one prostate disease expression profile map as described herein for use as comparison template. Preferably, the expression profile map is digital information stored in a computer-readable medium.

Instructions for using the kit according to one or more methods of the invention may comprise instructions for processing the prostate tissue sample and/or performing the test, instructions for interpreting the results as well as a notice in the form prescribed by a governmental agency (e.g., FDA) regulating the manufacture, use or sale of pharmaceuticals or biological products.

Screening of Candidate Compounds

As noted above, sets of genes whose expression profiles correlate with one or more selected prostate disease characteristics (e.g., prostate cancer progression) are attractive targets for identification of new therapeutic agents (e.g., via screens to detect compounds or entities that inhibit or enhance expression of these genes and/or their products). Accordingly, the present invention provides methods for the identification of compounds potentially useful for modulating prostate cancer progression.

As will be appreciated by those of ordinary skill in the art, any kind of compounds or agents can be tested using the inventive screening methods. A candidate compound may be a synthetic or natural compound; it may be a single molecule, a mixture of different molecules or a complex of at least two molecules. In certain embodiments, the inventive methods are used for testing one or more compounds. In other embodiments, the inventive methods are used for screening collections or libraries of compounds. As used herein, the term "collection" refers to any set of compounds, molecules or agents, while the term "library" refers to any set of compounds, molecules or agents that are structural analogs.

Libraries of candidate compounds that can be screened using the methods of the present invention may be either prepared or purchased from a number of companies. Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means.

Cells to be used in the practice of the screening methods of the present invention may be primary cells, secondary cells, or immortalized cells (e.g., established cell lines). They may be prepared by techniques well known in the art (for example, cells may be obtained by fine needle biopsy from a patient or a healthy donor) or purchased from immunological and microbiological commercial resources (for example, from the American Type Culture Collection, Manassas, Va.). Alternatively or additionally, cells may be genetically engineered to contain, for example, a gene of interest.

Selection of a particular cell type and/or cell line to perform an assay according to the present invention will be governed by several factors including the intended purpose of the assay. For example, an assay developed for primary drug screening (i.e., first round(s) of screening) may preferably be performed using established cell lines, which are commercially available and usually relatively easy to grow, while an assay to be used later in the drug development process may preferably be performed using primary or secondary cells, which are often more difficult to obtain, to maintain, and/or to grow than immortalized cells but which represent better experimental models for in vivo situations.

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Reproducibility of the results may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested. Generally, candidate compound concentrations from 1 fM to about 10 mM are used for screening. Preferred screening concentrations are generally between about 10 pM and about 100 µM.

The screening methods of the invention will provide "hits" or "leads", i.e., compounds that possess a desired but not optimized biological activity. Lead optimization performed on these compounds to fulfill all physicochemical, pharmacokinetic, and toxicologic factors required for clinical usefulness may provide improved drug candidates. The present invention also encompasses these improved drug candidates and their use as therapeutics for modulating prostate cancer progression.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented in this section have been described by the Applicants in a recent scientific publication (T. A. Bismar et al., "Defining Aggressive Prostate Cancer Using a 12 Gene Model", Neoplasia, January 2006, accepted for publication). This paper is incorporated herein by reference in its entirety.

EXAMPLE 1

12 Gene Model

Materials and Methods

Case Selection

A prostate cancer progression microarray (TMA) has previously been developed in the Applicants' laboratory in order to test biomarkers (M. A. Rubin et al., Am. J. Pathol., 2004, 164: 831-840, which is incorporated herein by reference in its entirety). This TMA is composed of benign prostate tissue, localized prostate cancer, hormone naïve, and hormone refractory metastatic prostate cancer. These cases came from well-fixed radical prostatectomy, lymph node, and metastatic prostate cancer specimens from the University of Michigan (Ann Arbor, Mich.), the University Hospital Ulm (Ulm, Germany), and the rapid autopsy program University of Michigan Specialized Program of Research Excellence (S.P.O.R.E.) in prostate cancer (M. A. Rubin et al., Clin. Cancer Res., 2000, 6: 1038-1045, which is incorporated herein by reference in its entirety). All samples were collected with prior Institutional Review Board approval at each respective institution.

Selection of Biomarkers for Immunohistochemistry

The majority of the biomarkers for this study derived from a large scale proteomics study where more than 1383 proteins were screened (S. Varambally et al., "Integrative genomic and proteomic analysis of prostate cancer reveals signatures of metastatic progression", Cancer Cell, 2005, 8: 393-406, which is incorporated herein by reference in its entirety). Refinement of this list of proteins included coordinate over or under expression by cDNA expression array analysis (D. R. Rhodes et al., Cancer Res., 2002, 62: 4427-4433; D. R. Rhodes et al., Neoplasia, 2004, 6: 1-6; D. R. Rhodes et al., J. Natl. Cancer Inst., 2003, 95: 661-668; and D. R. Rhodes et al., Proc. Natl., Acad. Sci., USA, 2004, 101: 9309-9314).

The initial selection process identified 50 dysregulated proteins of which 41 were optimized for in situ tissue evaluation by immunohistochemistry on archival formalin-fixed, paraffin-embedded material (S. Varambally et al., Cancer Cell, 2005, 8: 393-406).

The 41 biomarkers are presented in Table 3. This list includes Prostate Specific Antigen (PSA) (B. S. Stein et al., Urology, 1984, 24:146-152; P. N. Brawn et al., Cancer, 1991, 68:1592-1599), Alpha-Methylacyl CoA Racemase (AMACR) (J. Xu et al., Cancer Res., 2000, 60:1677-1682; Z. Jiang et al., Am. J. Surg. Pathol., 2001, 25: 1397-1404; M. A. Rubin et al., JAMA, 2002, 287: 1662-1670; J. Luo et al., Cancer Res., 2002, 62: 2220-2226; R. Kuefer et al., Am. J. Pathol., 2002, 161: 841-848), E-Cadherin (M. J. Bussemakers et al., Cancer Res., 1992, 52: 2916-2922; T. Otto et al., Urol. Res., 1993, 21: 359-362; R. Umbas et al., Cancer Res., 1992, 52: 5104-5109; A. M. De Marzo et al., Urology, 1999, 53:707-713; M. A. Rubin et al., Hum. Pathol., 2001, 32: 690-697); p27 (Y. Guo et al., Clin. Cancer Res., 1997, 3: 2269-2274; J. C. Cheville et al., Mod. Pathol., 1998, 11: 324-328; C. Cordon-Cardo et al., J. Natl. Cancer Inst., 1998, 90: 1284-1291; J. Tsihlias et al., Cancer Res., 1998, 58: 542-548; R. M. Yang et al., J. Urol., 1998, 159: 941-945); Fatty Acid Synthase (FAS) (J. I. Epstein et al., Urology, 1995, 45: 81-86; M. S. Shurbaji et al., Hum. Pathol., 1996, 27: 917-921; J. V. Swinnen et al., Int. J. Cancer, 2002, 98:19-22; A. Baron et al., J. Cell Biochem., 2004, 91:47-953; L. Bubendorf et al., J. Pathol., 1996, 178: 437-441; A. R. Botticelli et al., Eur. J. Histochem., 1998, 42: 41-48; L. Bubendorf et al., Hum. Pathol., 1998, 29: 949-954) and the Androgen Receptor (AR) (E. P. Gelmann, J. Clin. Oncol., 2002, 20: 3001-3015).

This list also includes biomarkers that have been more recently associated with prostate cancer such as E2F (C. Park et al., Carcinogenesis, 2001, 22: 1727-1731; L. Farhana et al., Cancer Res., 2002, 62: 3842-3849; X Mu and C. Chang, J. Biol. Chem., 2003, 278: 42840-42845; C. S. Foster et al., Oncogene, 2004, 23: 5871-5879); Enhancer of Zeste 2 (EZH2) (D. R. Rhodes et al., J. Natl. Cancer Inst., 2003, 95: 661-668; A. P. Bracken et al., EMBO J., 2003, 22: 5323-5335; S. Varambally et al., Nature, 2002, 419: 624-629; C. G. Kleer et al., Proc. Natl. Acad. Sci. USA, 2003, 100: 11606-11611); Jagged 1 (D. B. Martin et al., Cancer Res., 2004, 64: 347-355; S. Santagata et al., Cancer Res., 2004, 64: 6854-6857); MTA1 (S. Varambally et al., Nature, 2002, 419: 624-629; M. D. Hofer et al., Cancer Res., 2004, 64: 825-829); p63 (S. Signoretti el al., Am. J. Pathol., 2000, 57: 1769-1775; J. K. Parsons et al., Urology, 2001, 58: 619-624; L. D. Davis et al., Anticancer Res., 2002, 22: 3819-3825); Zinc alpha-2-glycoprotein (ZAC) (J. Lapointe J et al., Proc. Natl. Acad. Sci. USA, 2004, 101: 811-816; L. P. Hale et al., Clin. Cancer Res., 2001, 7: 846-853); MUC1 (J. Lapointe et al., Proc. Natl. Acad. Sci. USA, 2004, 101: 811-816; A. Kirschenbaum et al., Mol. Urol., 1999, 3: 163-168); X-linked inhibitor of apoptosis (XIAP) (T. Nomura et al., Urol. Res., 2003, 31: 37-44; C. P. Ng and B. Bonavida, Mol. Cancer Ther., 2002, 1: 1051-1058), which has also been recently associated with prostate cancer progression; Tumor protein D 52 (TPD52), a candidate oncogene, identified in the 8q21 amplicon was recently identified to be associated with prostate cancer progression, and the development of hormone refractory prostate cancer (C. P. Ng and B. Bonavida, Mol. Cancer Ther., 2002, 1: 1051-1058; M. L. Cher et al., Genes Chromosomes Cancer, 1994, 11: 153-162; J. A. Macoska et al., Urology, 2000, 55: 776-782: J. A. Macoska et al., Cancer Res., 1994, 54: 3824-3830: J. A. Macoska et al., Cancer Res., 1995, 55: 5390-5395; J. A. Macoska et al., Genes Chromosomes Cancer, 1993, 8: 88-97; R. Wang et al., Cancer Res., 2004, 64: 1589-1594; M. A. Rubin et al., Cancer Res., 2004, 64: 3814-3822).

The remaining biomarkers have not been specifically associated with prostate cancer progression. These include ABP280, JAM1, BM28, Fatty Acid Synthase (FAS), a protein that had been known to be over-expressed in prostate cancer and consistently seen to be over expressed in expression array studies (D. R. Rhodes et al., Cancer Res., 2002, 62: 4427-4433; M. S. Shurbaji et al., Hum. Pathol., 1996, 27: 917-921; A. Baron et al., J. Cell Biochem., 2004, 91: 47-53).

Several of the markers selected for analysis have been associated with cancer outcome such as E-Cadherin dysregulation (R. Umbas et al., Cancer Res., 1992, 52: 5104-5109; A. M. De Marzo et al., Urology, 1999, 53: 707-713; R. Umbas et al., Cancer Res., 1994, 54: 3929-3933) and XIAP (K. S. Krajewska et al., Clinical Cancer Research, 2003, 9: 4914-4925). Also included are some other biomarkers that have previously been reported to be associated with prostate cancer but were not identified in the screening study, such as Kruppel-like factor 6 (KLF6), as it was reported to have a high level of LOH and mutations in prostate cancer (G. Narla et al., Science, 2001, 294: 2563-2566).

Quantitative Biomarkers Analysis

The majority of the biomarkers for this study derived from a large scale proteomics study where more than 1383 proteins were screened (S. Varambally et al., Cancer Cell, 2005, 8: 393-406). Protein expression was evaluated by immunohistochemistry using an automated quantitative image analysis system, ACIS II (Chromavision Medical Systems, Inc., San Juan Capistrano, Calif.). The ACIS II consists of a microscope with a computer controlled mechanical stage. Proprietary software is used to detect the brown stain intensity of the chromogen used for the immunohistochemical analysis and to compare this value to the intensity of the blue counter stain used as background. Intensity levels are recorded as Intensity Units ranging from 0 to 255. The reproducibility of the ACIS II system was tested and confirmed by scoring of the same TMA on separate occasions ($r^2$=0.973, data not shown).

Given the heterogeneity of the prostate tissue samples, the study pathologists used a computer-based selection tool to highlight areas within each 0.6 mm core for analysis. To account for this heterogeneity, four tissue cores were evaluated for each case. In cases where less than three cores where available, the data was substituted with the median value of the biomarker for that histologic subtype. The missing values can arise both from corrupted core sections (i.e., technically inadequate) and from a change of diagnosis. Missing values were present in the dataset 98 times in benign (13.3%), 130 times in localized prostate cancer (17.6%) and 6 times in the metastatic prostate cancer samples (0.8%). The change of histologic diagnosis was not a rare event and therefore supports the need to review all TMA cores. As a pooling strategy, the mean TMA core value was adapted for each patient.

Figure 5:
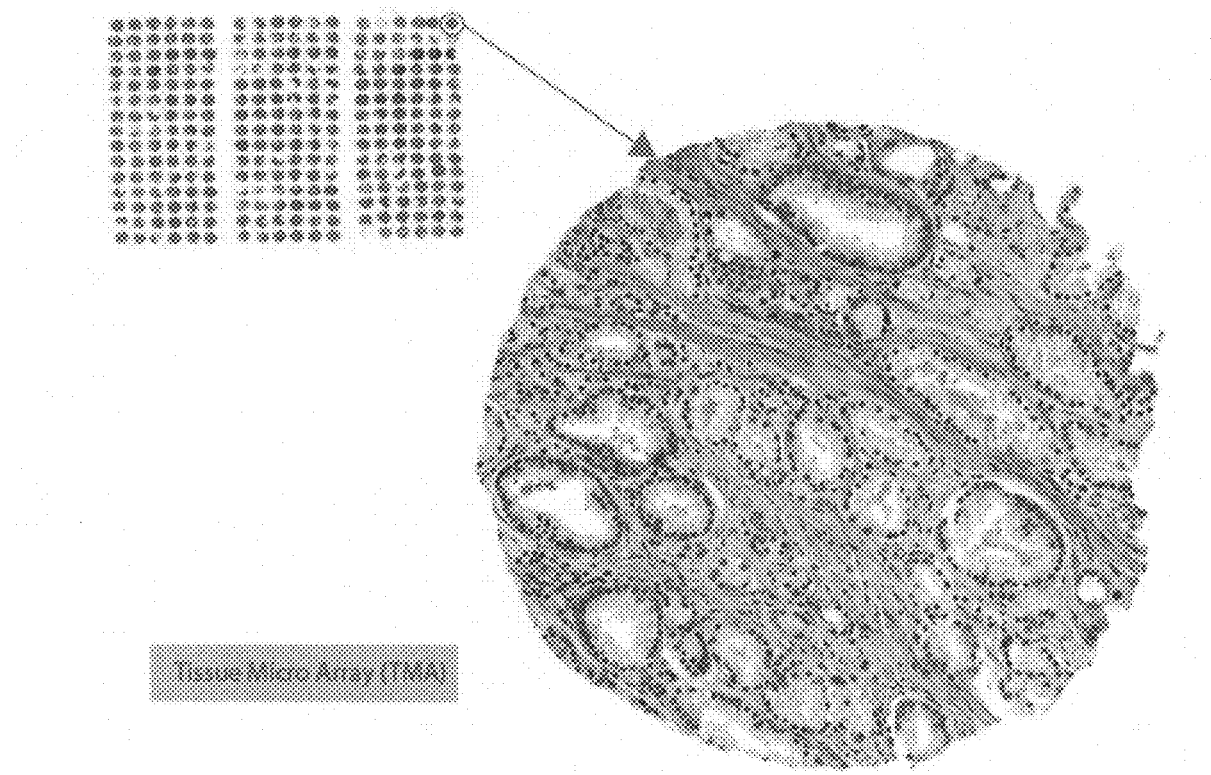
FIG. 5 presents examples of hemotoxylin and eosin stained images from the prostate cancer progression tissue array.

The diagnosis of the selected area was recorded in the database as either benign, localized prostate cancer or metastatic prostate cancer. Cores with only stroma or non-diagnostic areas were excluded from further analysis. The hemotoxylin and eosin stained images from this tissue array are presented on FIG. 5.

Statistical Analysis

Clustering. Hierachical agglomerative clustering both on samples and genes separately was carried out using Pearson correlation as similarity measure and average linkage method (M. B. Eisen et al., Proc. Natl. Acad. Sci. USA, 1998, 95: 14863-14868). Clustering was performed using dChip software (C. Li and W. H. Wong, Proc. Acad. Sci. USA, 2001, 98: 31-36).

Linear Discriminant Analysis (LDA). LDA was applied on the dataset of 41 genes to select genes (H. Jiang et al., BMC Bioinformatics, 2004, 5: 81; R. A. Johnson and D. W. Wichern, "Applied Multivariate Statistical Analysis", 2002, 5$^{th}$ Ed., Prentice Hall: Upper Saddle River, N.J.), which discriminates among the diagnostic groups. Discriminant analysis uses both multivariate analysis of variance and discriminant procedure to identify a linear combination of predictor variables that best characterizes the differences among the groups. LDA computes the so-called canonical variables (or canonical discriminant functions). The first canonical variable is the linear combination of the variables that maximizes the differences between the means of the groups (one dimension). The second canonical variable represents the maximum dispersion of the means in a direction that is orthogonal to the first canonical variable.

The other canonical variables are generated in a similar manner. The number of canonical variables is given by the number of groups minus 1. Therefore, in the present study with five tissue classes (i.e., benign, localized prostate cancer, hormone naïve metastatic prostate cancer, hormone refractory metastatic prostate cancer, and metastatic small cell prostate cancer), there are 4 canonical variables. When the two first canonical variables account for a large proportion of the variability in the dataset, a good graphical representation of the group differences can be obtained plotting the data along the first and the second canonical variables.

By applying a stepwise approach (adding and removing variables on variance evaluation), the most powerful subset of predicting variables can be defined. Stepwise selection begins by identifying the variable for which the means are most different and continues by adding the next best variable stepwise. Wilks' lambda method was used to control the entry or removal of predictor variables from the discriminant function. In discriminant analysis, prior probabilities were computed from group sizes. To measure the degree of success of the classification accuracy was evaluated. LDA was performed using R (R. Ihaka and R. R. Gentleman, Journal of Computational and Graphical Statistics, 1996, 5:299-314) and SPSS (SPSS Inc., Chicago, Ill.).

Validation using Expression Array Analysis. Expression data from a well annotated, publicly available dataset of 80 localized prostate tumors was obtained (G. V. Glinsky et al., J. Clin. Invest., 2004, 113: 913-923). Features representing the 12 genes identified in the protein expression analysis were determined for U95Av2 microarrays and mapped to U133A microarrays using the "Best match" table provided by Affymetrix (www.affymetrix.com/index.affx). Clustering was performed using dChip software as described above (C. Li and W. H. Wong, Proc. Natl. Acad. Sci. USA, 2001, 98: 31-36). The two major clusters determined using the first branch point of the dataset (C0 and C1) were identified and a chi-square test was performed to determine if the distribution between C0 and C 1 was non-random with respect to clinical outcome (PSA failure versus non failure). These two clusters (C0 vs. C1) along with observed class (non-recurrent vs. recurrent) and time to outcome (censorship or recurrence) were imported into GraphPad Prism to generate a Kaplan Meier plot and calculate the log rank statistic.

Results

Selection of Genes for Analysis

Using a high throughput proteomic screen of prostate tissue extracts, a panel of 50 proteins that were differentially expressed were identified from over 1383 proteins (S. Varambally et al., Cancer Cell, 2005, 8: 393-406). In prior work, this panel was evaluated by Western blot analysis and the candidate proteins that best distinguish between benign prostate tissue, localized cancer, and metastatic prostate cancer were selected for further analysis. Further selection required that these proteins were also concordantly dysregulated at the transcriptome level as previously described (S. Varambally et al., Cancer Cell, 2005, 8: 393-406). Antibodies against 41 of these proteins were obtained that also worked on formalin-fixed paraffin embedded tissue samples.

Immunohistochemistry was performed on a prostate cancer progression tissue microarray (TMA) that has been previously described and consists of benign prostate tissue, clinically localized prostate cancer, hormone naïve metastatic prostate cancer, and hormone refractory metastatic prostate cancer (M. A. Rubin et al., Am. J. Pathol., 2004, 164: 831-840). The immunohistochemical staining intensity was scored using an automated image analysis system. Protein expression of these genes with mean staining intensity scores and 95% confidence intervals (CI) are presented in Table 1.

Hierachical Clustering Results

Figure 1A:
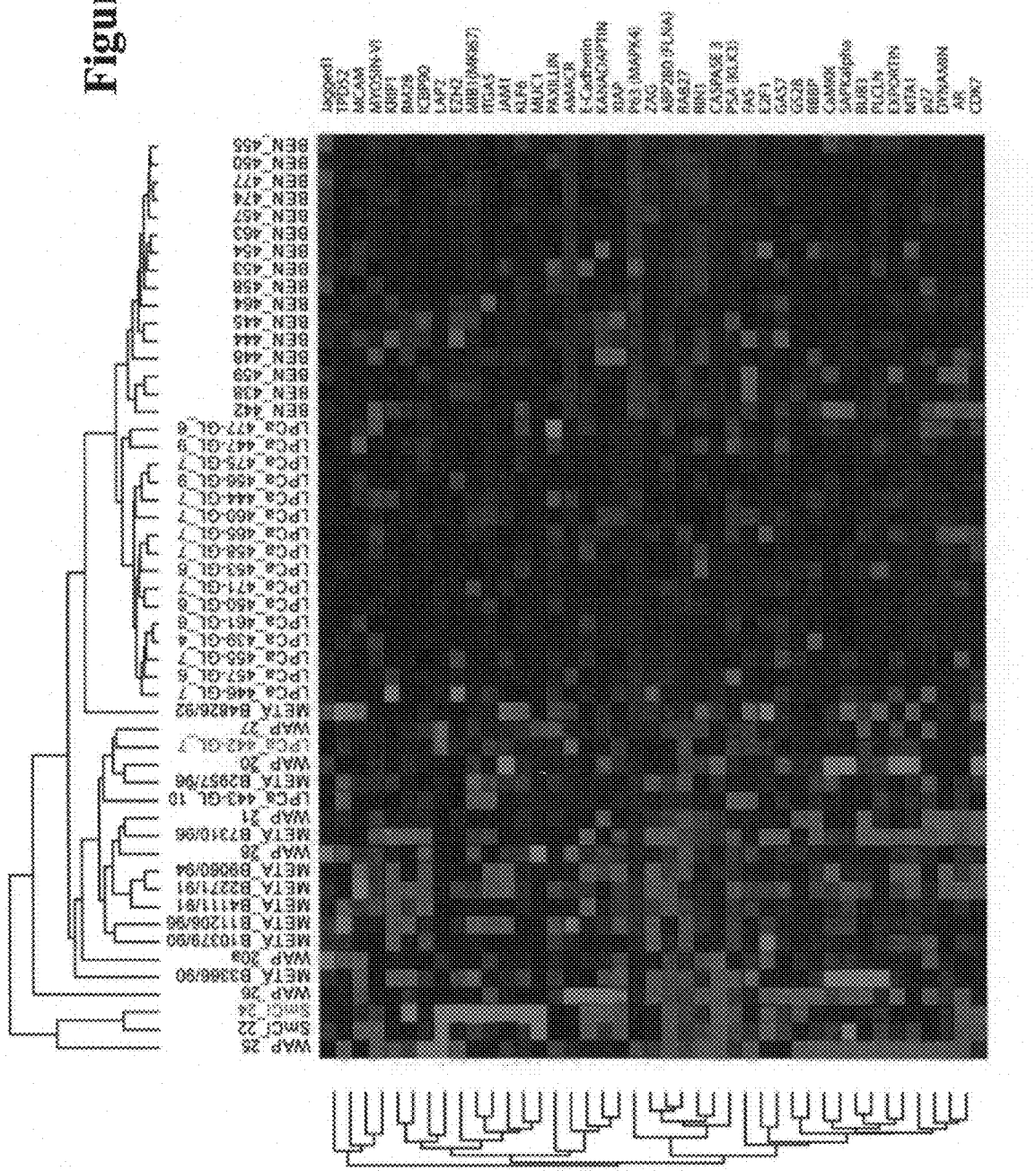
FIG. 1(A) is a "heat map" showing the relative protein expression of these 41 genes. Protein expression was determined using antibodies directed against the various gene products and measured by immunohistochemistry. The protein expression was determined using a semi-automated image analysis system ASCIS II (Chromavision), which measures staining intensity along a continuous scale from 0 to 255. Low expression and high expression are depicted using light green and bright red, respectively. Hierarchical clustering of the samples demonstrates good but not perfect ability of this 41 gene panel to distinguish between the different classes.
Figure 1B:
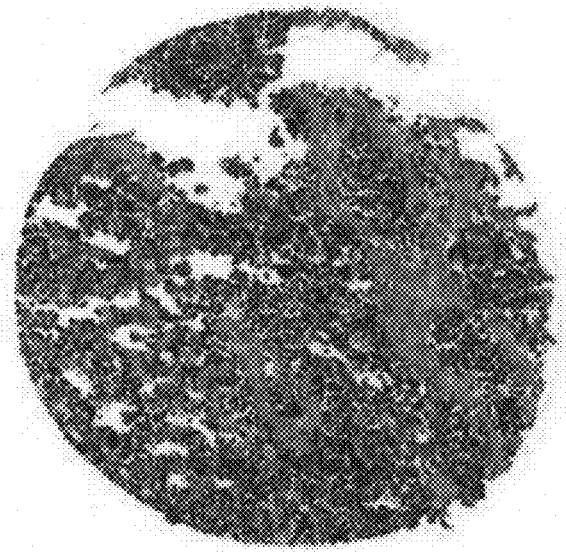
FIG. 1(B) presents two hemotoxylin and eosin stained images. This figure demonstrates that while some sub-types of metastatic prostate cancer (small cell cancer, upper part, 200× original magnification) had discrete profiles, the clustering did not accurately distinguish between all of the hormone naïve and hormone refractory prostate tumor samples. Interestingly, a high-grade, clinically localized prostate cancer (Gleason pattern 4 prostate cancer, lower part, 200× original magnification) was found to cluster more closely to the metastatic samples using this 41 gene profile.
Figure 2A:
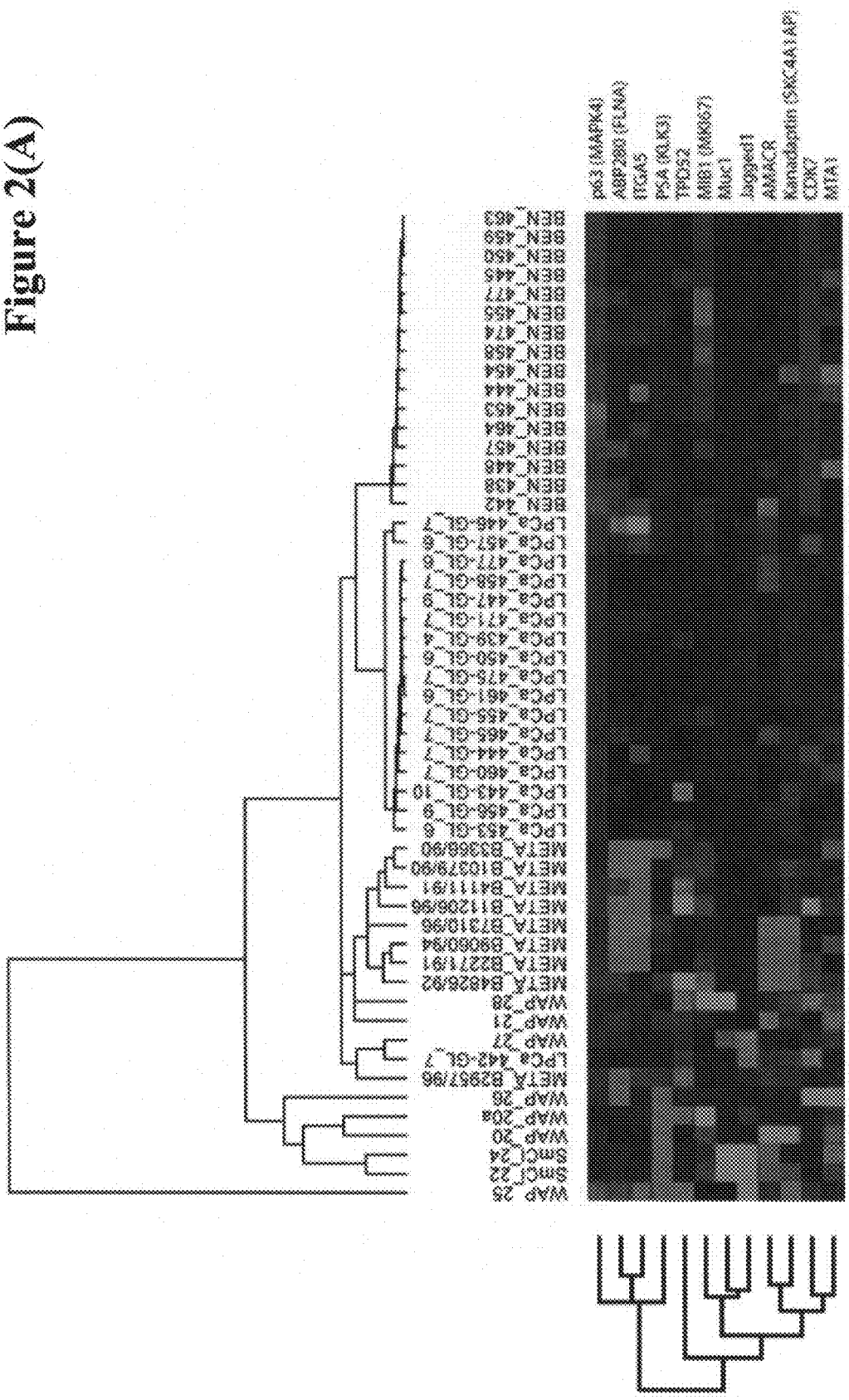
FIG. 2(A) shows the heat map of the 12 genes that best predict prostate cancer progression as identified by stepwise linear discriminant analysis (LDA).
Figure 2B:
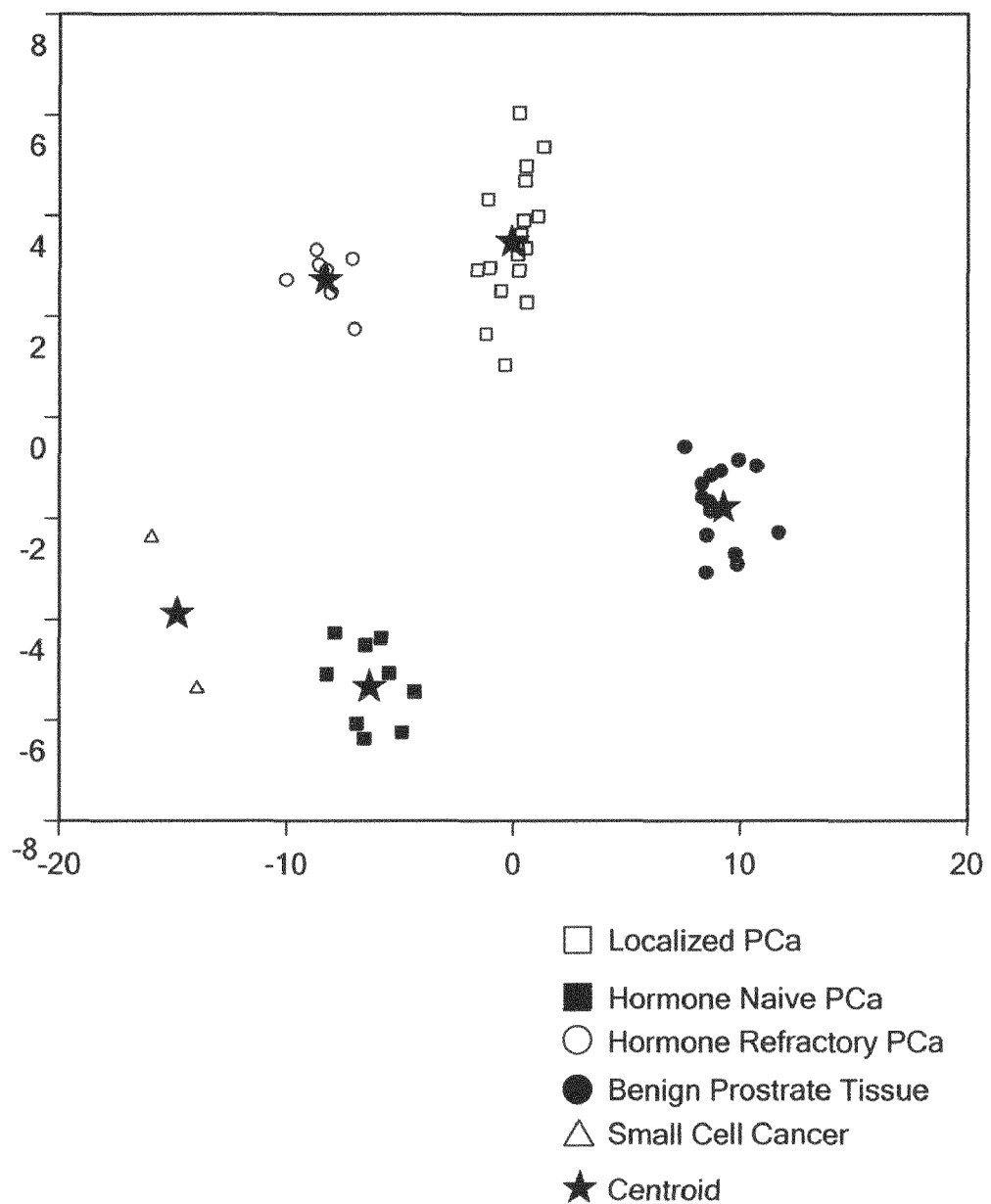
FIG. 2(B) is a graph presenting the cases along the first and second canonical components of the LDA, which account for a cumulative variance of 87.9%. The discriminative power of the 12 gene model was not decreased with respect to the 41 gene model, confirming the redundancy of information provided by some genes.

High level analysis was performed to check data quality present in the set of the 41 selected proteins. In particular, through hierarchical clustering, it was verified if sufficient protein expression data could distinguish different states of prostate disease. Clustering was separately carried out on the samples and the 41 proteins. Highest levels of the sample tree (FIG. 1A) demonstrated good separation between aggressive prostate cancer states and clinically localized prostate cancer (LPCa). The clustering also reliably distinguished benign prostate tissue (BEN) from clinically localized prostate cancer (LPCa). Although the metastatic tumors clustered together, no clear subclusters were found for hormone naïve (META) and hormone refractory metastatic tumors (WAP), as demonstrated in FIG. 1A. Two cases of metastatic small cell prostate cancer (SM_CL) clustered together (FIG. 2B, top image). A sample of localized prostate cancer (LPCa__442-GL__7) was naturally grouped with the metastatic tumors. Although the overall Gleason score for this case was 7, the sample analyzed for this study depicted in FIG. 1B demonstrates pure Gleason pattern 4 prostate cancer consistent with a high-grade tumor.

Figure 1B:

When clustering genes based on samples, it is notably a group of seven genes over-expressed in benign tissues and under-expressed in aggressive cancer (i.e., p63, ZAG, ABP280, RAB27, RIN1, CASPASE3, and PSA). Extreme over and under expression of these proteins are present for aggressive cancer types (FIG. 1, right side), supporting the hypothesis that the investigated set of markers might distinguish aggressive from indolent prostate cancer. The heat map also suggests that some genes provide redundant or partially redundant information, as confirmed by descriptive statistics presented in Table 1.

Linear Discriminant Analysis

In order to verify the discriminative power of the genes in terms of cancer progression and to identify gene profiles specific for localized prostate cancer and advanced prostate cancer, a predictive model was developed based on protein expression. Linear Discriminant Analysis (LDA) was applied to identify a linear combination of predictor variables that best characterizes the differences among the groups. Clear separation of the groups was found as depicted in FIG. 2. The first and the second canonical variables cumulatively account for the 91.7% of the variance (68.1% and 23.6%, respectively). This result suggests that different groups (benign, localized cancer, hormone naïve metastases, hormone refractory metastases and small cells) are linearly separable in the gene space.

Stepwise linear discriminant analysis identified a set of 12 genes from the original set of 41 studied genes that best predicted tumor progression (Table 2) using 52 cases. FIG. 2B represents the cases along the first and second canonical components, which account for a cumulative variance of 87.9%. The discriminative power of the 12 gene model was not decreased with respect to the 41 gene model, confirming also the redundancy of information provided by some genes; alternative subsets of genes from the 41 gene set could be selected. Even though the model accuracy evaluated by cross validation (both using training and test sets ⅔ to ⅓ and leave-one-out) was very good, reliable performances should be assessed on a different larger dataset.

Expression Array Validation

The genes identified from the original proteomics screen were selected because they demonstrated either over or under expression at both the protein and transcriptional level (S. Varambally et al., Cancer Cell, 2005, 8: 393-406). In the study presented here this discriminatory panel has been refined to 12 genes. In order to determine if RNA expression of these 12 genes could discriminate between local prostate cancers that progress following radical prostatectomy from those that do not, a previously published dataset of 80 tumors was analyzed (G. V. Glinsky et al., J. Clin. Invest., 2004, 113: 913-923, which is incorporated herein by reference in its entirety). In an approach described by Ramaswami et al. (Nat. Genet., 2003, 33: 49-54), the dChip software was used to develop a hierarchical cluster of all samples using the expression of features representing the 12 genes included in the present model or 15 features on U133A (FIG. 3A).

Figure 3B:
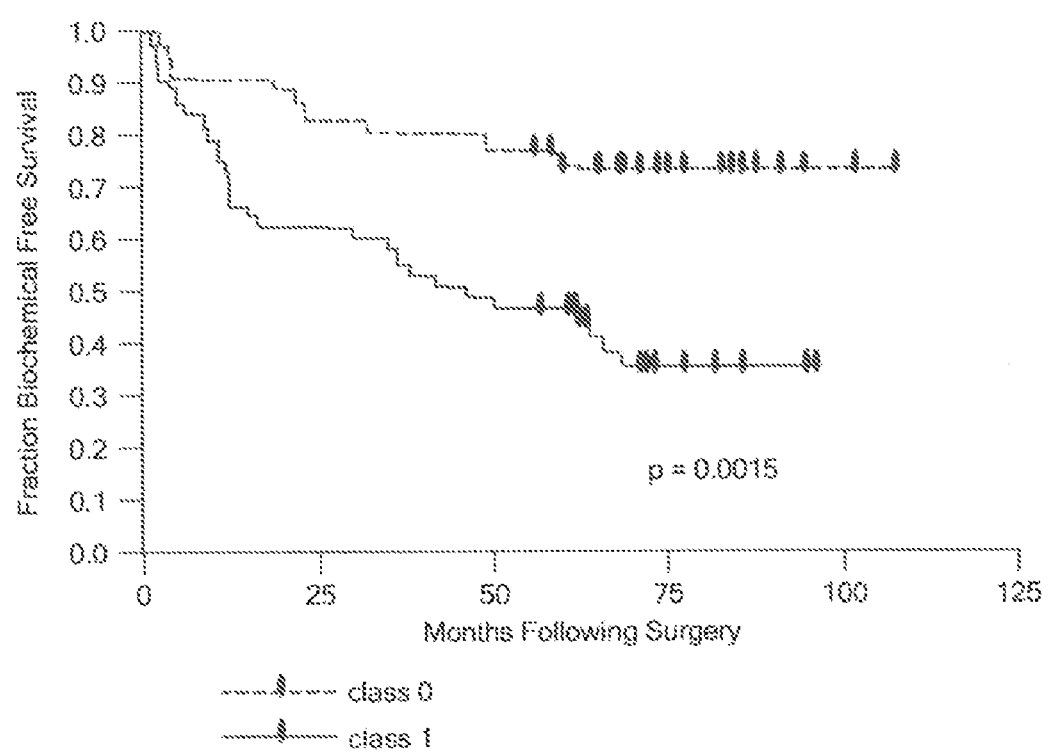
FIG. 3(B) is a graph showing the fraction of biochemical free survival as a function of months following surgery. When these major clusters (C0 and C1) were used as categorical variable to divide the set for Kaplan-Meier analysis, significant separation was observed between samples within the two clusters with respect to PSA failure following surgery (p=0.0015). Thus, RNA expression of this group of genes also appears to distinguish between localized tumors likely to be aggressive from those that are cured by surgery.
Figure 4:
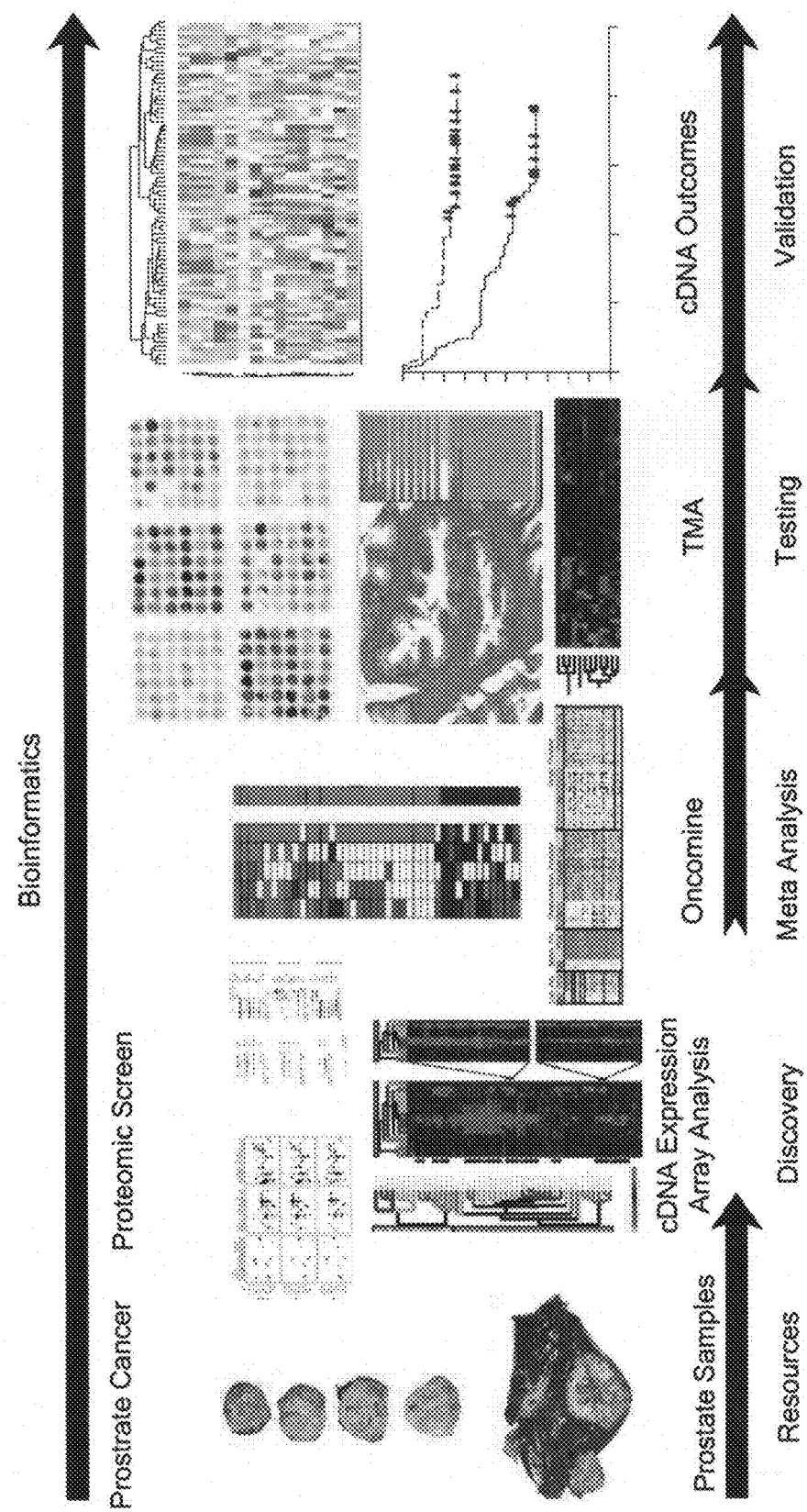
FIG. 4 is a scheme showing the different stages of biomarker development used in the present study. The first critical step was the identification of high quality samples in order to perform high throughput analysis including proteomics and expression array analysis. In this study a wide range of prostate cancer samples were used from several sources. A meta analysis was performed to ensure that the genes identified in one study were genes that also have been determined to be dysregulated in other studies. The data was then tested using tissue microarrays (TMAs) with the goal of developing a robust model. In the study presented here a panel of 12 genes was determined. This panel of genes was then validated on an independent data set to discriminate aggressive from indolent forms of prostate cancer. Throughout the entire process, bioinformatics was required to prioritize and refine the molecular models.

When the 80 cases were clustered using dChip, recurrent and non-recurrent samples were non-randomly distributed between the two major clusters (p<0.01) (FIG. 3A). When these major clusters (C0 and C1) were used as a categorical variable to divide the set for Kaplan-Meier analysis (FIG. 3B), significant separation was observed between samples within the two clusters with respect to PSA failure following surgery (p=0.0015). Thus, RNA expression of this group of genes also appears to distinguish between localized tumors likely to be aggressive from those that cured by surgery.

Discussion

Prostate cancer progression is a complex process involving many genes and pathways (M. A. Rubin and A. M. De Marzo, Mod. Pathol., 2004, 17: 380-388; A. M. De Marzo et al., Lancet 2003, 361: 955-964). Although some alterations may be critical in the early development of the disease (e.g., 8p loss), more advanced metastatic prostate cancers exhibit numerous molecular alterations that may not be causative but instead seen later in the progression as a consequence of genetic instability (e.g., PTEN mutations). It is also evident from multiple expression array studies that the genes identified to distinguish different disease states such as cancer versus benign tumor may differ. This may be due to different molecular platforms, the samples used in the investigation, treatment effects, or analytic approach used.

One approach in the development of a robust model has been to examine which genes are consistently differentially regulated from experiment using a meta-analysis of expression array data (D. R. Rhodes et al., Cancer Res., 2002, 62: 4427-2233; D. R. Rhodes et al., Neoplasia, 2004, 6: 1-6). In the study presented here, such an approach was used to focus on genes that were consistently dysregulated both at the protein and expression array level. This has now led to a focused model including 12 genes from a starting point of over 1383 genes used in the initial proteomics screen (S. Varambally et al., Cancer Cell, 2005, 8: 393-406). It is intriguing that this 12 gene model of prostate cancer progression initially developed using a TMA was able to distinguish patients with clinically localized prostate cancer that were at highest risk to develop PSA-failure following surgery. This testing and validation study crossed platforms but was still able to predict outcome on an entirely independent clinical cohort.

Large numbers of genes also might predict outcome. However, as seen in the analysis of microarray studies, there are many redundant genes. The reason for associated gene expression patterns may be explained by the activation of similar molecular pathways or general processes such as proliferation or apoptosis. This observation would support the view that one should in fact be surprised if all studies came up with the same stets of genes. For example, in the current study, after removing the 12 gene model from the original 41 genes, other good models can be identified with the remaining genes. Therefore, the approach used in the present study should be considered as a paradigm to identify predictive gene sets but should not be viewed as the only possible solution.

This study further supports the view that most of the large molecular profiles have redundancy built into them. Methods such as the Integrative Proteomic and Genomic Analysis demonstrate how critical it is to develop strategies to refine large gene sets (S. Varambally et al, Cancer Cell, 2005, 8: 393-406). Other methods such as Gene Set Enrichment Analysis (S. Monti et al., Blood, 2005, 105: 1851-1861; V. K. Mootha et al., Nat. Genet., 2003, 34: 267-273) can also help define pathways of dysregulated genes allowing us to focus on sets of genes or gene interactions as opposed to list of non-annotated genes.

In summary, a model of prostate cancer progression has been developed using a multi-stage approach. The first selection process sorted through over 1383 genes by evaluating a combination of cDNA expression array analysis and a high throughput proteomic screen, which led to the identification of 50 differentially expressed genes. The second stage described herein tested a prostate cancer progression model using a quantitative analysis of protein expression using immunohistochemistry on a tissue microarray. This led to a 12 gene model that was validated on a separate patient cohort using PSA-failure following surgery for clinically localized prostate cancer as the endpoint. This study demonstrates that cross platform models can lead to predictive models. More importantly, this smaller model can be more easily used in a clinical setting. Future work will test this model in a prospective manner.

EXAMPLE 2

Validation of the 12 Gene Model

The 12 gene model disclosed herein (which consists of ABP280 (FLNA), AMACR, CDK7, ITGA5, JAGGED1, KANADAPTIN, MIB1 (MKI67), MTA1, MUC1, p63, PSA (KLK3), and TPD52) and a 9 gene model consisting of AMACR, ITGA5, CIAP, KRIP1, DRBP76, OCCLUDIN, BM28, P62 and LAP2, were evaluated using a Swedish Watchful Waiting Cohort.

The Swedish Watchful Waiting Cohort used in this evaluation is the largest population-based watchful waiting cohort, and consists of patients from Örebro, Sweden and the Southeast region of Sweden with clinically localized prostate cancer, who underwent watchful waiting as initial therapy. This cohort initially described in 1989 (J. E. Johansson et al., Lancet, 1989, 1: 799-803) consists of men who all presented with voiding symptoms referred to the urology department to rule out the diagnosis of prostate carcinoma. From 1977 to 1991, 1498 patients were diagnosed with prostate cancer (240 in Örebro and 1258 in the Southeast region of Sweden). In accordance with standard practices at that time in Sweden, these patients were initially followed expectantly ("watchful waiting"). Patients were treated with androgen deprivation therapy only if they exhibited symptoms.

The baseline evaluation of these patients at diagnosis included physical examination, chest radiography, i.v. pyelogram, bone scan, and skeletal radiography (if needed). Lymph node staging was not done. Patient follow-up included clinical examinations, laboratory tests, and bone scans every 6 months during the first 2 years following the initial prostate cancer diagnosis and subsequently every 2 years. Medical records of all deceased patients have been reviewed to determine the cause of death. As a validation, the classification of cause of death was compared with that recorded in the Swedish Death Register. Thus far, agreement on cause of death has been >90%, with no evidence of systematic over- or underestimation of prostate cancer as cause of death.

Results of the follow-up for death and metastases through 2005 is presented in the table below.

|  | Örebro | SE | Total |
|---|---|---|---|
| Total cohort | 240 | 1258 | 1498 |
| Lethal phenotype (cancer death or metastases) | 43 | 199 | 242 |
| Long-term survivors (10 years without METS) | 63 | 250 | 313 |

In order to ensure a uniform review of the pathology, a study pathologist reviewed all cases. Uniform pathology review included Gleason grading, and other pathologic features. FIG. 6 presents the characteristics of the Örebro Watchful Waiting Cohort.

The tissue microarrays (TMA) for the Örebro cohort and SE region cohort were assembled using the manual tissue arrayer (Beecher Instruments, Silver Spring, Md.) as previously described (M. A Rubin et al., Am. J. Surg. Pathol., 2002, 26: 312-319). Tissue cores from circled areas were targeted for transfer to the recipient array blocks. Three to five replicate tissue cores were sampled from each patient sample. In all cases, the dominant prostate cancer nodule or the nodule with the highest Gleason pattern was sampled for the TMA. The 0.6-mm diameter TMA cores were each spaced at 0.8 mm from core-center to core-center. Each block was assembled without prior knowledge of associated clinical or pathology staging information. After construction, 4-μm sections were cut and stained with H&E on the initial slides to verify the histologic diagnosis. All data is maintained on a relational database as previously described (S. Manley et al., Am. J. Pathol., 2001, 159: 837-843)

A semi-automated quantitative image analysis system, ACIS II (Chromavision, San Juan Capistrano, Calif.), was used to evaluate the same TMA slides. The ACIS II device consists of a microscope with a computer-controlled mechanical stage. Proprietary software was used to detect the intensity of the chromogen used to stain proteins of interest and compares this value to blue counterstain used as background. Theoretical intensity levels range from 0 to 255 chromogen intensity units. In pilot experiments for this study, the reproducibility of the ACIS II system was tested and confirmed by scoring several TMAs on separate occasions.

Scores were developed for each individual in the cohort based on protein expression across the 9- and 12-gene models. Each signature was then assessed as predictor of outcome, adjusted for clinical factors, age, Gleason score, tumor stage using Cox regression.

Results of the validation are presented in FIGS. 8-11 and summarized in FIG. 12. The results obtained show that the molecular signatures are associated with an increased risk of death or metastases, independent of clinical parameters, and suggest that it is possible to identify signatures to distinguish lethal and indolent cancers.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims

What is claimed is:

1. A kit for diagnosing prostate disease in a subject, said kit comprising:
    a set of reagents that specifically detects expression levels of a set of genes comprising ABP280 (FLNA) and at least three or more of genes selected from the group consisting of AMACR, CDK7, ITGA5, JAGGED1, KANADAPTIN, MIB1 (MKI67), MTA1, MUC1, p63, PSA(KLK3), and TPD52; and
    instructions for using said kit for diagnosing prostate disease in the subject.

2. The kit of claim 1, wherein the set of reagents detects the expression of mRNA expressed from said set of genes.

3. The kit of claim 2, wherein the set of reagents comprises nucleic acid probes complementary to mRNA expressed from said set of genes.

4. The kit of claim 3, wherein the nucleic acid probes complementary to mRNA are cDNA or oligonucleotides.

5. The kit of claim 3, wherein the nucleic acid probes complementary to mRNA are immobilized on a substrate surface.

6. The kit of claim 1, wherein the set of reagents detects the expression of polypeptides encoded by said set of genes.

7. The kit of claim 6, wherein the set of reagents comprises antibodies that specifically bind to the polypeptides encoded by said set of genes.

8. The kit of claim 1, wherein the kit further comprises one prostate disease expression profile map.

9. The kit of claim 1, wherein the set of genes comprises ABP280 (FLNA) and at least four or more of genes selected from the group consisting of AMACR, CDK7, ITGA5, JAGGED1, KANADAPTIN, MIB1 (MKI67), MTA1, MUC1, p63, PSA(KLK3), and TPD52.

10. The kit of claim 1, wherein the set of genes comprises ABP280 (FLNA) and at least five or more of genes selected from the group consisting of AMACR, CDK7, ITGA5, JAGGED1, KANADAPTIN, MIB1 (MKI67), MTA1, MUC1, p63, PSA(KLK3), and TPD52.

11. The kit of claim 1, wherein the set of genes comprises ABP280 (FLNA) and at least six or more of genes selected from the group consisting of AMACR, CDK7, ITGA5, JAGGED1, KANADAPTIN, MIB1 (MKI67), MTA1, MUC1, p63, PSA(KLK3), and TPD52.

12. The kit of claim 1, wherein the set of genes comprises ABP280 (FLNA) and at least seven or more of genes selected from the group consisting of AMACR, CDK7, ITGA5, JAGGED1, KANADAPTIN, MIB1 (MKI67), MTA1, MUC1, p63, PSA(KLK3), and TPD52.

13. The kit of claim 1, wherein the set of genes comprises ABP280 (FLNA) and at least eight or more of genes selected from the group consisting of AMACR, CDK7, ITGA5, JAGGED1, KANADAPTIN, MIB1 (MKI67), MTA1, MUC1, p63, PSA(KLK3), and TPD52.

14. The kit of claim 1, wherein the set of genes comprises ABP280 (FLNA) and at least nine or more of genes selected from the group consisting of AMACR, CDK7, ITGA5, JAGGED1, KANADAPTIN, MIB1 (MKI67), MTA1, MUC1, p63, PSA(KLK3), and TPD52.

15. The kit of claim 1, wherein the set of genes comprises ABP280 (FLNA) and at least ten or more of genes selected from the group consisting of AMACR, CDK7, ITGA5, JAGGED1, KANADAPTIN, MIB1 (MKI67), MTA1, MUC1, p63, PSA(KLK3), and TPD52.

16. The kit of claim 1, wherein the set of genes comprises ABP280 (FLNA), AMACR, CDK7, ITGA5, JAGGED1, KANADAPTIN, MIB1 (MKI67), MTA1, MUC1, p63, PSA (KLK3), and TPD52.

17. A kit for providing a prognosis for prostate disease in a subject, said kit comprising:
   a set of reagents that specifically detects expression levels of a set of genes comprising ABP280 (FLNA) and at least three or more of genes selected from the group consisting of AMACR, CDK7, ITGA5, JAGGED1, KANADAPTIN, MIB1 (MKI67), MTA1, MUC1, p63, PSA(KLK3), and TPD52; and
   instructions for using said kit for providing a prognosis for prostate disease in the subject.

18. The kit of claim 17, wherein the set of reagents detects the expression of mRNA expressed from said set of genes.

19. The kit of claim 18, wherein the set of reagents comprises nucleic acid probes complementary to mRNA expressed from said set of genes.

20. The kit of claim 19, wherein the nucleic acid probes complementary to mRNA are cDNA or oligonucleotides.

21. The kit of claim 19, wherein the nucleic acid probes complementary to mRNA are immobilized on a substrate surface.

22. The kit of claim 17, wherein the set of reagents detects the expression of polypeptides encoded by said genes.

23. The kit of claim 22, wherein the set of reagents comprises antibodies that specifically bind to polypeptides encoded by said set of genes.

24. The kit of claim 17, further comprising at least one prostate disease expression profile map.

25. The kit of claim 17, wherein the set of genes comprises ABP280 (FLNA) and at least four or more of genes selected from the group consisting of AMACR, CDK7, ITGA5, JAGGED1, KANADAPTIN, MIB1 (MKI67), MTA1, MUC1, p63, PSA(KLK3), and TPD52.

26. The kit of claim 17, wherein the set of genes comprises ABP280 (FLNA) and at least five or more of genes selected from the group consisting of AMACR, CDK7, ITGA5, JAGGED1, KANADAPTIN, MIB1 (MKI67), MTA1, MUC1, p63, PSA(KLK3), and TPD52.

27. The kit of claim 17, wherein the set of genes comprises ABP280 (FLNA) and at least six or more of genes selected from the group consisting of AMACR, CDK7, ITGA5, JAGGED1, KANADAPTIN, MIB1 (MKI67), MTA1, MUC1, p63, PSA(KLK3), and TPD52.

28. The kit of claim 17, wherein the set of genes comprises ABP280 (FLNA) and at least seven or more of genes selected from the group consisting of AMACR, CDK7, ITGA5, JAGGED1, KANADAPTIN, MIB1 (MKI67), MTA1, MUC1, p63, PSA(KLK3), and TPD52.

29. The kit of claim 17, wherein the set of genes comprises ABP280 (FLNA) and at least eight or more of genes selected from the group consisting of AMACR, CDK7, ITGA5, JAGGED1, KANADAPTIN, MIB1 (MKI67), MTA1, MUC1, p63, PSA(KLK3), and TPD52.

30. The kit of claim 17, wherein the set of genes comprises ABP280 (FLNA) and at least nine or more of genes selected from the group consisting of AMACR, CDK7, ITGA5, JAGGED1, KANADAPTIN, MIB1 (MKI67), MTA1, MUC1, p63, PSA(KLK3), and TPD52.

31. The kit of claim 17, wherein the set of genes comprises ABP280 (FLNA) and at least ten or more of genes selected from the group consisting of AMACR, CDK7, ITGA5, JAGGED1, KANADAPTIN, MIB1 (MKI67), MTA1, MUC1, p63, PSA(KLK3), and TPD52.

32. The kit of claim 17, wherein the set of genes comprises ABP280 (FLNA), AMACR, CDK7, ITGA5, JAGGED1, KANADAPTIN, MIB1 (MKI67), MTA1, MUC1, p63, PSA (KLK3), and TPD52.

* * * * *